(12) United States Patent
Pan

(10) Patent No.: US 7,405,081 B2
(45) Date of Patent: Jul. 29, 2008

(54) METHODS AND KITS FOR IDENTIFYING SCAVENGERS OF REACTIVE OXYGEN SPECIES (ROS)

(76) Inventor: Shen Q. Pan, 107 Clements Road #06-02, Singapore (SG) 129790

( * ) Notice: Subject to any disclaimer, the term of this patent is extended or adjusted under 35 U.S.C. 154(b) by 0 days.

(21) Appl. No.: 10/467,104

(22) PCT Filed: Feb. 5, 2002

(86) PCT No.: PCT/SG02/00018

§ 371 (c)(1),
(2), (4) Date: Aug. 4, 2003

(87) PCT Pub. No.: WO02/063032

PCT Pub. Date: Aug. 15, 2002

(65) Prior Publication Data

US 2004/0072218 A1 Apr. 15, 2004

Related U.S. Application Data

(60) Provisional application No. 60/266,657, filed on Feb. 5, 2001.

(51) Int. Cl.
*C12N 15/85* (2006.01)
*C12N 15/63* (2006.01)
(52) U.S. Cl. .................. 435/455; 435/320.1; 435/325; 536/24.1
(58) Field of Classification Search .................. 435/4, 435/6, 455, 468, 471, 440, 325, 419, 254.11
See application file for complete search history.

(56) References Cited

U.S. PATENT DOCUMENTS

| | | | |
|---|---|---|---|
| 5,491,084 A | 2/1996 | Chalfie et al. | |
| 5,585,232 A | 12/1996 | Farr | |
| 5,585,252 A | 12/1996 | Wong et al. | |
| 5,589,337 A | 12/1996 | Farr | |
| 5,731,163 A | 3/1998 | Vandyk et al. | |
| 5,811,231 A * | 9/1998 | Farr et al. ...................... | 435/6 |
| 5,955,275 A | 9/1999 | Kamb | |
| 6,753,146 B1 * | 6/2004 | Bernstein ...................... | 435/6 |
| 2002/0015940 A1 * | 2/2002 | Rao et al. ...................... | 435/4 |

FOREIGN PATENT DOCUMENTS

| WO | WO 00/49876 | * | 8/2000 |
|---|---|---|---|
| WO | WO 01/25400 | | 4/2001 |

OTHER PUBLICATIONS

Albano et al. J. Biomol. Screen. 2001; 6:421-428.*
Baker et al. Experientia. 1996; 52:597-9.*
Hartsfield et al. FASEB J. 1998; 12:1675-82.*
Lavrovsky et al. Mech. Ageing Dev. 2000; 114:49-6.*
Lewis. Somatic Cell Mol. Genet. 1985; 11:319-24.*
Martinez et al. J. Bact. 1997; 179:5188-5194.*
Santos et al. Mol. Mic. 1999; 32:789-98.*
Shakelford et al. Free Radical Bio. Med. 2000; 28:1387-04.*
Tsujimoto et al. J. Bact. 2000 ; 182 :5121-26.*
Morel et al. (Molecular Pharmacology, 2000, vol. 57, pp. 1158-1164).*
Xu et al (Molecular Microbiology, 2000, vol. 35, pp. 407-414).*
Ansley, J.C., Georgina, A.D., and Huw, D.W. (1995) Evidence for cell-density dependent regulation of catalase activity in *Rhizobium leguminosarum* bv. *phaseoli. Microbiology* 141: 843-851.
Arnold et al. (2001) *Proc. Natl. Acad. Sci. USA*, 98(10): 5550-55.
Bagyan, I., Casillas-Martinez, L., and Setlow, P. (1998) The *katX* gene, which codes for the catalase in spores of *Bacillus subtilis*, is a forespore-specific gene controlled by $\sigma^F$, and KatX is essential for hydrogen peroxide resistance of the germinating spore. *J Bacteriol* 180: 2057-2062.
Baker, J. and Orlandi, E.W. (1995) Active Oxygen in Plant pathogenesis. *Annu Rev Phytopathol* 33: 299-321.
Bishai, W.R., Smith, H.O., and Barcak, G.J. (1994) A peroxide/ascorbate-inducible catalase from *Haemophilus influenzae* is homologous to the *Escherichia coli katE* gene product. *J Bacteriol* 176: 2914-2921.
Bravo, J., Fita, I., Gouet, P., Jouve, H.M., Melik-adamyan, W., and Murshudov, G.N. (1997) in *Oxidative stress and the molecular biology of antioxidant defenses*. Scandalios, J.G. (eds). Cold Spring Harbor Laboratory Press, pp. 407-445.
Bsat, N., Herbig,A. Casillas-Martinez, L., Setlow, P., and Helmann, J.D. (1998) *Bacillus subtilis* contains multiple Fur homologues: identification of the iron uptake (Fur) and peroxide regulon (PerR) repressors. *Mol Microbiol* 29: 189-198.
Cangelosi, G.A., Best, E.A., Martinetti, G. and Nester, E.W. (1991) Genetic analysis of *Agrobacterium*. *Methods Enzymol* 204: 384-397.
Charles, T.C., and Nester, E.W. (1993) A chromosomally encoded two-component sensory transduction system is required for virulence of *Agrobacterium tumefaciens*. *J Bacteriol* 175: 6614-6625.
Chen, C.Y., and Winans, S.C. (1991) Controlled expression of the transcriptional activator gene *virG* in *Agrobacterium tumefaciens* by using the *Escherichia coli lac* promoter. *J Bacteriol* 173: 1139-1144.
Chen, L., Keramati, L., and Helmann, J.D. (1995) Coordinate regulation of *Bacillus subtilis* peroxide stress genes by hydrogen peroxide and metal ions. *Proc Natl Acad Sci* 92: 8190-8194.

(Continued)

*Primary Examiner*—Celine Qian
(74) *Attorney, Agent, or Firm*—Biexh, Stewart, Kolasch & Birch, LLP

(57) ABSTRACT

This invention relates to methods and kits for determining the level of $H_2O_2$ inside a cell, and for determining whether a test compound has ability to scavenge a reactive oxygen species (ROS). The methods and diagnostic kits of this invention employ a cell containing a promoter which is inducible by an ROS, such as the $H_2O_2$-inducible KatA promoter of *Agrobacterium tumefaciens*. The methods of this invention may also be used to select for new or improved ROS scavengers by expressing a library of test scavengers in cells which express a reporter from a ROS-inducible promoter and selecting for those cells whose level of ROS-inducible expression of the reporter is reduced.

14 Claims, 10 Drawing Sheets

OTHER PUBLICATIONS

Christman, M.F, Storz, G., and Ames, B.N. (1989) OxyR, a positive regulator of hydrogen peroxide-inducible genes in *Escherichia coli* and *Salmonella typhimurium*, is homologous to a family of bacterial regulatory proteins. *Proc Natl Acad Sci* 86: 3484-3488.

Clare, D.A., Duong, M.N., Darr, D., Archibald, F. and Fridovich, I. (1984) Effects of molecular oxygen on detection of superoxide radical with nitroblue tetrazolium and on activity stains for catalase. *Anal Biochem* 140: 532-537.

Ditta, G., Stanfield, S., Corbin, D. and Helinski, D.R. (1980) Broad host range DNA cloning system for gram-negative bacteria: construction of a gene bank of *Rhizobium melioti. Proc Natl Acad Sci* 77: 7347-7351.

Engelmann, S., Lindner, C., and Hecker, M. (1995) Cloning, nucleotide sequence, and regulation of *katE* encoding a $\sigma^B$-dependent catalase in *Bacillus subtilis. J Bacteriol* 177: 5598-5605.

Fang, F.C., Libby, S.J., Buchmeier, N.A., Loewen, P.C., Switala, J., Harwood, J. and Guiney, D.G. (1992) The Alternative σ Factor KatF (RpoS) Regulates *Salmonella* Virulence *Proc Natl Acad Sci* 89: 11978-11982.

Farr et al., Microbiol. Rev., 55, pp. 561-585 (1991).

Foster, J.W (1999) When protons attack: microbiol strategies of acid adaptation. *Current Opinion in Microbiology* 2: 170-174.

Gonzalez-Flecha, B. and Demple, B. (1995) Metabolic sources of hydrogen peroxide in aerobically growing *Escherichia coli. J Biol Chem* 270: 13681-13687.

Gonzalez-Flecha, B. and Demple, B. (1997) Homeostatic regulation of intracellular hydrogen peroxide concentration in aerobically growing *Escherichia coli. J Bacteriol* 179:382-388.

Gort and Imlay, (1998) *J Bacteriol.* Mar. 1998 180(6):1402-10.

Gould S. J., and Subramani, S., *Anal Biochem.* Nov. 1988 15;175(1):5-13.

Greenberg et al., *Proc. Natl. Acad. Sci. USA*, 87, pp. 6181-6185 (1990).

Gregory, E.M., and Fridovich, I. (1974) Visualization of catalase on acrylamide gels. *Anal Biochem* 58: 57-62.

Hahn, J.S., Oh, S.Y., and Roe, J.H. (2000) Regulation of the *furA* and *catC* operon, encoding a ferric uptake regulator homologue and catalase-peroxidase, respectively, in *Streptomyces coelicolor* A3(2). *J Bacteriol* 182: 3767-3774.

Hertel, C., Schmidt, G., Fischer, M., Oellers, K., and Hammes, W.P. (1998) Oxygen-dependent regulation of the expression of the catalase gene *katA* of *Lactobacillus sakei* LTH677. *Appl Environ Microbiol* 64: 1359-1365.

Herouart, D., Sigaud, S., Moreau, S., Frendo, P., Touati, D., and Puppo, A. ( 1996) Cloning and characterization of the *katA* gene of *Rhizobium melioti* encoding a hydrogen peroxide-inducible catalase. *J Bacteriol* 178: 6802-6809.

Hillar, A., et al., (2000) Biochemistry 39: 5868-5875.

Ho, S.N., Hunt, H.D., Horton, R.M., Pullen, J.K., and Pease, L.R. (1989) Site-directed mutagenesis by overlap extension using the polymerase chain reaction. *Gene* 77: 51-59.

Imlay, J.A., and Linn, S. (1988) DNA damage and oxygen radical toxicity. *Science* 240: 1302-1309.

Jia, Y.H., Li, L.P. Hou, Q.M. and Pan, S.Q. (2002) An *Agrobacterium* chromosomal gene involved in tumorigenesis encodes a homolog of a *Rhizobium* outer membrane protein. *Gene* 284: 113-124.

Kogoma et al., Proc. Natl. Acad. Sci USA, 85, pp. 4799-4803 (1988).

Koh J., Enders G. H., et al, Nature. Jun. 8; 375(6531):506-10 (1995).

Kullik, I., Toledano, M.B., Tartaglia, L.A., and Storz, G. (1995) Mutational analysis of the redox-sensitive transcriptional regulator OxyR: regions important for oxidation and transcriptional activation. *J Bacteriol* 177: 1275-1284.

Laochumroonvorapong, P., Paul S, Manca, C., Freedman, V.H., and Kaplan, G. (1997) Mycobacterial growth and sensitivity to $H_2O_2$ killing in human monocytes in vitro. *Infect Immun* 65: 4850-4857.

Levine, A., Tenhaken, R., Dixon, R. and Lamb, C. (1994) $H_2O_2$ from the oxidative burst orchestrates the plant hypersensitive disease resistance response. *Cell* 79: 583-593.

Li, L.P., Li, Y., Lim, T.M., and Pan, S.Q. (1999) GFP-aided confocal laser scanning microscopy can monitor *Agrobacterium tumefaciens* cell morphology and gene expression associated with infection. *FEMS Microbiol Lett* 179: 141-146.

Loewen, P.C. (1997) Bacterial catalases. In *Oxidative stress and the molecular biology of antioxidant defenses*. Scandalios, J.G. (eds). Cold Spring Harbor Laboratory Press, pp. 273-308.

Loewen, P.C., and Hengge-Aronis, R. (1994) The role of the sigma factor sigma S (KatF) in bacterial global regulation. *Annu Rev Microbiol* 48: 53-80.

Loewen, P.C., and Triggs, B.L. (1984) Genetic mapping of *katF*, a locus that with *katE* affects the synthesis of a second catalase species in *Escherichia coli. J Bacteriol* 160: 668-675.

Loprasert, S., Vattanaviboon, P., Praituan, W., Chamnongpol, S., and Mongkolsuk, S. (1996) Regulation of the oxidative stress protective enzymes, catalase and superoxide dismutase in *Xanthomonas. Gene* 179: 33-37.

Ma, M., and Eaton, J.W. (1992) Multicellular oxidant defense in unicellular organisms. *Proc. Natl. Acad. Sci.* 89: 7924-7928.

Maciver, I., and Hansen, E.J. (1996) Lack of expression of the global regulator OxyR in *Haemophilus influenzae* has a profound effect on growth phenotype. *Infect Immun* 64: 4618-4629.

Mahadev et al. (2001) *J. Biol. Chem.* 15;276(24):21938-42. Abstract.

Mantis N.J.,and Winans, S.C. (1992) The *Agrobacterium tumefaciens vir* gene transcriptional activator *virG* is transcriptionally induced by acid pH and other stress stimuli. *J. Bacteriol* 174: 1189-1196.

Melov, S., Ravenscroft, J., Malik, S., Gill, M.S., Walker, D.W., Clayton, P.E., Wallace, D.C., Malfroy, B., Doctrow, S.R., and Lithgow, G.J. (2000) Extension of life-span with superoxide dismutase/catalase mimetics. *Science* 289: 1567-1569.

Mohanty, J. Jonathan, G., Jaffe, S., Schulman E. S., and Raible, D.G. (1997) A highly sensitive fluorescent micro-assay of $H_2O_2$ release from activated human leukocytes using a dihydroxyphenoxazine derivative. *J Immunol Methods* 202: 133-141.

Olson, E.R. (1993) Influence of pH on bacterial gene expression. *Mol Microbiol* 8: 5-14.

Pagan-Ramos, E., Song, J., McFalone, M., Mudd, M.H., and Deretic, V. (1998) Oxidative stress response and characterization of the *oxyR-ahpC* and *furA-katG* loci in *Mycobacterium marinum. J Bacteriol* 180: 4856-4864.

Ren et al. (2002) *J. Biol. Chem.* 277(1):559-65.

Rocha, E.R. and Smith, C.J. (1995) Biochemical and genetic analyses of a catalase from the anaerobic bacterium *Bacteroides fragilis. J Bacteriol* 177: 3111-3119.

Rocha, E.R., and Smith, C.J. (1997) Regulation of *Bacteriodes fragilis katB* mRNA by oxidative stress and carbon limitation. *J Bacteriol* 179: 7033-7039.

Saliim and Abu-Shakra (2001) *Teratog Carcinog Mutagen* 21(5):349-59.

Schellhorn, H.E. (1995) Regulation of hydroperoxidase (catalase) expression in *Escherichia coli. FEMS Microbiol Lett* 131: 113-119.

Schellhorn, H.E., and Hassan, H.M. (1988) Transcriptional regulation of *katE* in *Escherichia coli* K-12. *J Bacteriol* 170: 4286-4292.

Shapira S. K., Chou J., et al., Gene Nov.; 25: 71-82 (1983).

Storz, G, Tartaglia, L.A., and Ames, B.N. (1990) Transcriptional regulator of oxidative stress-inducible genes: direct activation by oxidation. *Science* 248: 189-194. Abstract.

Storz, G., and Tartaglia, L.A. (1992) OxyR: a regulator of antioxidant genes. *J Nutr* 122: 627-630. Abstract.

Storz, G.,and Imlay, J.A. (1999) Oxidative stress. *Curr Opin Microbiol* 2: 188-194.

Suarez, A., Guttler, A., Stratz, M., Staendner, L.H., Timmis, K.N., and Guzman, C.A. (1997) Green fluorescent protein-based reporter systems for genetic analysis of bacteria including monocopy applications. *Gene* 196: 69-74.

Tao, K., Makino, K., Yonei, S., Nakata, A., and Shinagawa, H. (1991) Purification and characterization of the *Escherichia coli* OxyR protein, the positive regulator for a hydrogen peroxide-inducible regulon. *J Biochem* 109: 262-266.

Tao, K., Makino, K., Yonei, S., Nakata, A., and Shinagawa, H., (1989) Molecular cloning and nucleotide sequencing of *oxyR*, the positive regulatory gene of a regulon for an adaptive response to oxidative stress in *Escherichia coli*: homologies between OxyR protein and a family of bacterial activator proteins. *Mol Gen Genet* 218: 371-316.

Thiel G., Petersohn D., and Schoch S., Gene Feb. 12; 168: 173-176 (1996).

Winans, S.C. (1990) Transcriptional induction of an *Agrobacterium* regulatory gene at tandem promoters by plant-released phenolic compounds, phosphate starvation, and acidic growth media. *J Bacteriol* 172: 2433-2438.

Wojtaszek, P. (1997) Oxidative burst: an early plant response to pathogen infection. *Biochem J* 322: 681-692.

Xu, W.Q. and Pan, S.Q. (2000) An *Agrobacterium* catalase as a virulence factor involved in tumorigenesis. *Mol Microbiol* 2:407-14. Abstract.

Zheng, M., Doan, B., Schneider, T.D., and Storz, G. (1999) OxyR and SoxRS regulation of *fur*. *J Bacteriol* 181: 4639-4643.

Zhu et al. (2000) Journal of Bacteriology 182:3885-3895.

Zou, P., Borovok, I., Ortiz de Orue Lucana D, Muller, D., and Schrempf, H. (1999) The mycelium-associated *Streptomyces reticuli* catalase-peroxidase, its gene and regulation by FurS. *Microbiology*. 145: 549-59.

Schellhorn, H.E., "Regulation of hydroperoxidase (catalase) expression in *Escherichia coli*", *FEMS Microbiology Letters 131*, pp. 113-119 (1995).

Nunoshiba, Tatsuo, "A cluster of constitutive mutations affecting the C-terminus of the Redox-sensitive SoxR transcriptional activator", *Nucleic Acids Research*, vol. 22, No. 15, pp. 2958-2962 (1994).

Tartaglia, Louis A, et al., "Identification and Molecular Analysis of the oxyR-Regulated Promoters Important for the Bacterial Adaptation to Oxidative Stress", *J. Mol. Biol.*, vol. 210, pp. 709-719 (1989).

Engelmann, Susanne, et al., "Impaired oxidative stress resistance of *Bacillus subtilis* sigB mutants and the role of katA and katE", *FEMS Microbiology Letters 145*, pp. 63-69 (1996).

Prieto-Alamo, et al., "Transcriptional Regulation of Glutaredoxin and Thioredoxin Pathways and Related Enzymes in Response to Oxidative Stress", *The Journal of Biological Chemistry*, vol. 275, No. 18, pp. 13398-13405, (May 5, 2000).

Howell, Michael L., et al. "AnkB, a Periplasmic Ankyrin-Like Protein in *Pseudomonas aeruginosa*, Is Required for Optimal Catalase B (KatB) Activity and Resistance to Hydrogen Peroxide", *Journal of Bacteriology*, pp. 4545-4556 (Aug. 2000).

Greenberg, Jean T., et al., "Positive control of a global antioxidant defense regulon activated by superoxide-generating agents in *Escherichia coli*", *Proc. Natl. Acad. Sci. USA*, vol. 87, pp. 6181-6185 (Aug. 1990).

Wood, Timothy I., et al., "Interdependence of the position and orientation of SoxS binding sites in the transcriptional activation of the class 1 subset of *Escherichia coli* superoxide-inducible promoters", *Molecular Microbiology*, vol. 34(3), pp. 414-430 (1999).

Marquis, John C., et al., "Complex Genetic Response of Human Cells to Sublethal Levels of Pure Nitric Oxide", *Cancer Research*, pp. 3435-3440 (Aug. 1, 1998).

Baas, Arnold S., et al., "Differential Activation of Mitogen-Activated Protein Kinases by $H_2O_2$ and $O_2$-in Vascular Smooth Muscle Cells", *Circulation Research*, vol. 77, pp. 29-36 (1977).

Fawcett, William P., et al., "Purification of a MalE-SoxS fusion protein and identification of the control sites of *Escherichia coli* superoxide-inducible genes", *Molecular Microbiology*, vol. 14 (4), pp. 669-679 (1994).

Yang, Lan, et al., "Interaction of the τ2 Transcriptional Activation Domain of Glucocorticoid Receptor with a Novel Steroid Receptor Coactivator, Hic-5, Which Localizes to Both Focal Adhesions and the Nuclear Matrix", *Molecular Biology of the Cell*, vol. 11, pp. 2007-2018 (Jun. 2000).

Mongkolsuk, Skorn, et al., "Heterologous Growth Phase- and Temperature-Dependent Expression and $H_2O_2$ Toxicity Protection of a Superoxide-Inducible Monofunctional Catalase Gene from *Xanthomonas oryzae* pv. *oryzae*", *Journal of Bacteriology*, vol. 178, No. 12, pp. 3578-3584 (Jun. 1996).

Immenschuh, Stephan, et al., "Gene Regulation of Heme Oxygenase-1 as a Therapeutic Target", *Biochemical Pharmacology*, vol. 60, pp. 1121-1128 (2000).

Lu, Tze-Hong, et al., "Regulation of expression of the human heme oxygenase-1 gene in transfected chick embryo liver cell cultures", *Biochimica et Biophysica Acta*, vol. 1352, pp. 293-302 (1997).

Hangaishi, Misako, et al., "Induction of Heme Oxygenase-1 Can Act Protectively against Cardiac Ischemia/Reperfusion in Vivo", *Biochemical and Biophysical Research Communications*, vol. 279, pp. 582-588 (2000).

Tsujimoto, Yoshiyuki, et al., "Cooperative Regulation of DOG2, Encoding 2-Deoxyglucose-6-Phosphatase, by Snf1 Kinase and the High-Osmolarity Glycerol-Mitogen-Activated Protein Kinase Cascade in Stress Responses of *Saccharomyces cerevisiae*", *Journal of Bacteriology*, vol. 182, No. 18, pp. 5121-5126 (2000).

Meilhac, Oliver, et al., "Lipid peroxides induce expression of catalase in cultured vascular cells", *Journal of Lipid Research*, vol. 41, pp. 1205-1213 (2000).

Wakai, Matsakazu, et al., "An immunohistochemical study of the neuronal expression of maganese superoxide dismutase in sporadic amyotrophic lateral sclerosis", *Acta Neuropathology*, vol. 88, pp. 151-158 (1994).

Cho, Min Kyung, et al., "Induction of class α gluthathione S-transferases by 4-methylthiazole in the rat liver: role of oxidative stress", *Toxicology Letters*, vol. 115, pp. 107-115 (2000).

Brenneisen, Peter, et al., "Hydrogen Peroxide ($H_2O_2$) Increases the Steady-State mRNA Levels of Collagenase/MMP-1 in Human Derman Fibroblasts", *Free Radical Biology & Medicine*, vol. 22, No. 3, pp. 515-524 (1997).

Kelner, Michael J., et al., "Structural organization of the human gastrointestinal glutathione peroxidase (GPX2) promoter and 3'-nontranscribed region: transcriptional response to exogenous redox agents", *Gene*, vol. 248, pp. 109-116 (2000).

Kling, Peter G., "Involvement of Differential Metallothionein Expression in Free Radical Sensitivity of RTG-2 and CHSE-214 Cells", *Free Radical Biology & Medicine*, vol. 28, No. 11, pp. 1628-1637 (2000).

Sherman, David R., "Disparate responses to oxidative stress in saprophytic and pathogenic mycobacteria", *Proc. Natl. Acad. Sci. USA*, vol. 92, pp. 6625-6629 (Jul. 1995).

Ziemann, Christina, et al., "Reactive oxygen species participate in mdr1b mRNA and P-glycoprotein overexpression in primary rat hepatocyte cultures", *Carcinogenesis*, vol. 20, No. 3, pp. 407-414 (1999).

Mates, J.M., "Effects of antioxidant enzymes in the molecular control of reactive oxygen species toxicology", *Toxicology*, vol. 153, pp. 83-104 (2000).

Rocha, Edson, R., et al., "Role of the Alkyl Hydroperoxide Reductase (ahpCF) Gene in Oxidative Stress Defense of the Obligate Anaerobe *Bacteroides fragilis*", *Journal of Bacteriology*, pp. 5701-5710 (Sep. 1999).

Morgan, Robin W., et al., "Hydrogen peroxide-inducible proteins in *Salmonella typhimurium* overlap with heat shock and other stress proteins", *Proc. Natl. Acad. Sci. USA*, vol. 83, pp. 8059-8063 (Nov. 1986).

Jeong, Woojin, et al., Thioredoxin-dependent Hydroperoxide Peroxidase Activity of Bacterioferritin Comigratory Protein (BCP) as a New Member of the Thiol-specific Antioxidant Protein (TSA)/Alkyl Hydroperoxide Peroxidase C (AphC) Family, *The Journal of Biological Chemistry*, vol. 275, No. 4, pp. 2924-2930 (Jan. 28, 2000).

Rocha, Edson, et al., "The Redox-Sensitive Transcriptional Activator OxyR Regulates the Peroxide Response Regulon in the Obligate Anaerobe *Bacteroides fragilis*", *Journal of Bacteriology*, pp. 5059-5069 (Sep. 2000).

Yamamoto, Yuji, et al., "Cloning, Nucleotide Sequence, and Disruption of *Streptococcus* mutans Glutathione Reductase Gene (gor)", *Biosci. Biotechnol. Biochem*, vol. 63, No. 6, pp. 1056-1062 (1999).

* cited by examiner

FIG. 1

SEQUENCE LISTING

```
<160> NUMBER OF SEQ ID NOS: 5

<210> SEQ ID NO 1
<211> LENGTH: 522
<212> TYPE: DNA
<213> ORGANISM: Agrobacterium tumefaciens

<400> SEQUENCE: 1
ggcacgatcg cctatgacgt cgcgggtctg aagaccttcg gcttcgcctt cggccgcgaa      60
gacatctggg cgccggaaaa ggacacctat tggggtgacg aaaaggaatg gctggcgccg     120
agcgacggcc gttatggcga cgtgagcaag cccgagacgc tggaaaaccc gcttgccgcc     180
gtgcagatgg gcctgatcta cgtcaacccg gaaggtgtca acggcaagtc cgatccgctg     240
gcgacggcgg cgcagatgcg cgaaaccttt gcccgcatgg ggatggatga cgaggaaacc     300
gttgccctga cggccggcgg ccacaccatc ggcaagtccc atggcaatgg cagtgctgcc     360
aatctcagcc ccgatccgga agctgctggc ccggaatatc agggtctcgg ctggatcaat     420
accaagggcc gcggcattgg ccgtgacacc gtggtgtcgg gtatcgaagg cgcatggaca     480
agcgaaccaa ccaagtggga caacggcttc ttcgacatgc tg                        522
```

```
<210> SEQ ID NO 2
<211> LENGTH: 2839
<212> TYPE: DNA
<213> ORGANISM: Agrobacterium tumefaciens
<220> FEATURE:
<221> NAME/KEY: CDS
<222> LOCATION: (308)..(2476)

<400> SEQUENCE: 2
```

| | | | | | |
|---|---|---|---|---|---|
| aggctgggag | atggcgcagg | cttccgccgc | gcgcccgaaa | tggccgattt | tggccagcgc     60 |
| atcgaaataa | cggagatgtt | tcatggagag | ggcaatcata | agctcagcat | atcgcagcct    120 |
| ttagaatata | caattggaaa | ttatggaacc | cggctgttag | tcatcttcat | gacagaaaga    180 |
| agctgtagct | gtggatgatc | atcggcatcg | cagcaggtcg | tttgagacct | gccgctgcct    240 |
| ctggctcgga | atgctgcaca | tgtcgaactg | ataatttgtt | taattgctaa | tcccatcgga    300 |

```
gggcgaa atg gac gca act tca aaa ccg gct ggc aag tgt ccc gtc atg        349
        Met Asp Ala Thr Ser Lys Pro Ala Gly Lys Cys Pro Val Met
        1               5                   10 cat gga ggc aat acg gcc tcc ggc aaa tcg gtg acc gaa tgg tgg ccg        397
His Gly Gly Asn Thr Ala Ser Gly Lys Ser Val Thr Glu Trp Trp Pro
 15              20                  25                  30 aac gcg cta aac ctc gac atc ctg cat cag cac gac acc aag acc aat        445
Asn Ala Leu Asn Leu Asp Ile Leu His Gln His Asp Thr Lys Thr Asn
             35                  40                  45 ccg ctc ggc acc tcc ttc aac tac cgc gaa gcg ctg aag acg ctt gat        493
Pro Leu Gly Thr Ser Phe Asn Tyr Arg Glu Ala Leu Lys Thr Leu Asp
         50                  55                  60 gtc gaa gcc ctc aag gcc gat ctg cgc gcg ctt atg acc gac agc cag        541
Val Glu Ala Leu Lys Ala Asp Leu Arg Ala Leu Met Thr Asp Ser Gln
 65                  70                  75 gaa tgg tgg ccg gcc gac tgg ggc agt tat gtc ggc atg atg gcc cgt        589
Glu Trp Trp Pro Ala Asp Trp Gly Ser Tyr Val Gly Met Met Ala Arg
             80                  85                  90 gtt acc tgg cat gcc gcc ggt tcc tat cgt gtc aca gac ggt cgc ggc        637
Val Thr Trp His Ala Ala Gly Ser Tyr Arg Val Thr Asp Gly Arg Gly
 95                 100                 105                 110 ggc gcc aat acc ggc aac cag cgt ttt gca ccg ctc aat tcc tgg ccg        685
Gly Ala Asn Thr Gly Asn Gln Arg Phe Ala Pro Leu Asn Ser Trp Pro
                115                 120                 125 gac aac gtc aac acc gac aag ggc cgc cgc ctg ctg tgg ccg atc aag        733
Asp Asn Val Asn Thr Asp Lys Gly Arg Arg Leu Leu Trp Pro Ile Lys
            130                 135                 140 aag aaa tac ggc aac aag att tcc tgg gcc gac ctt atc gcg ctc gcc        781
Lys Lys Tyr Gly Asn Lys Ile Ser Trp Ala Asp Leu Ile Ala Leu Ala
        145                 150                 155 ggc acg atc gcc tat gac gtc gcg ggt ctg aag acc ttc ggc ttc gcc        829
Gly Thr Ile Ala Tyr Asp Val Ala Gly Leu Lys Thr Phe Gly Phe Ala
    160                 165                 170 ttc ggc cgc gaa gac atc tgg gcg ccg gaa aag gac acc tat tgg ggt        877
Phe Gly Arg Glu Asp Ile Trp Ala Pro Glu Lys Asp Thr Tyr Trp Gly
175                 180                 185                 190 gac gaa aag gaa tgg ctg gcg ccg agc gac ggc cgt tat ggc gac gtg        925
Asp Glu Lys Glu Trp Leu Ala Pro Ser Asp Gly Arg Tyr Gly Asp Val
                195                 200                 205 agc aag ccc gag acg ctg gaa aac ccg ctt gcc gcc gtg cag atg ggc        973
Ser Lys Pro Glu Thr Leu Glu Asn Pro Leu Ala Ala Val Gln Met Gly
            210                 215                 220 ctg atc tac gtc aac ccg gaa ggt gtc aac ggc aag tcc gat ccg ctg       1021
Leu Ile Tyr Val Asn Pro Glu Gly Val Asn Gly Lys Ser Asp Pro Leu
```

-continued

```
             225                 230                 235 gcg acg gcg gcg cag atg cgc gaa acc ttt gcc cgc atg ggg atg gat      1069
Ala Thr Ala Ala Gln Met Arg Glu Thr Phe Ala Arg Met Gly Met Asp
    240                 245                 250 gac gag gaa acc gtt gcc ctg acg gcc ggc cac acc atc ggc aag          1117
Asp Glu Glu Thr Val Ala Leu Thr Ala Gly Gly His Thr Ile Gly Lys
255                 260                 265                 270 tcc cat ggc aat ggc agt gct gcc aat ctc agc ccc gat ccg gaa gct      1165
Ser His Gly Asn Gly Ser Ala Ala Asn Leu Ser Pro Asp Pro Glu Ala
                275                 280                 285 gct ggc ccg gaa tat cag ggt ctc ggc tgg atc aat acc aag ggc cgc      1213
Ala Gly Pro Glu Tyr Gln Gly Leu Gly Trp Ile Asn Thr Lys Gly Arg
        290                 295                 300 ggc att ggc cgt gac acc gtg gtg tcg ggt atc gaa ggc gca tgg aca      1261
Gly Ile Gly Arg Asp Thr Val Val Ser Gly Ile Glu Gly Ala Trp Thr
            305                 310                 315 agc gaa cca acc aag tgg gac aac ggc ttc ttc gac atg ctg ttc aag      1309
Ser Glu Pro Thr Lys Trp Asp Asn Gly Phe Phe Asp Met Leu Phe Lys
    320                 325                 330 cac gag tgg acc ctg acg cac agc ccc gcg ggt gca tcg caa tgg gcg      1357
His Glu Trp Thr Leu Thr His Ser Pro Ala Gly Ala Ser Gln Trp Ala
335                 340                 345                 350 ccg att acc atc gcc gaa gaa gac aag cct gtt gat gtc gag gat gcg      1405
Pro Ile Thr Ile Ala Glu Glu Asp Lys Pro Val Asp Val Glu Asp Ala
                355                 360                 365 tcg atc cgc acc atc ccg atg atg acc gac gcc gac atg gcc ctg aag      1453
Ser Ile Arg Thr Ile Pro Met Met Thr Asp Ala Asp Met Ala Leu Lys
        370                 375                 380 gtc gat ccg atc tac cgc gag att tcg ctg aag ttc aag gac gat cag      1501
Val Asp Pro Ile Tyr Arg Glu Ile Ser Leu Lys Phe Lys Asp Asp Gln
            385                 390                 395 gac cat ttc tct gat gtc ttc gcc cgc gcc tgg ttc aag ctg acg cat      1549
Asp His Phe Ser Asp Val Phe Ala Arg Ala Trp Phe Lys Leu Thr His
    400                 405                 410 cgc gac atg ggg ccg aag tcc cgt tac gtc ggc ccg gat gtt ccg gct      1597
Arg Asp Met Gly Pro Lys Ser Arg Tyr Val Gly Pro Asp Val Pro Ala
415                 420                 425                 430 gaa gac ctg atc tgg cag gat ccg atc ccg gca ggc tcc acg agc tac      1645
Glu Asp Leu Ile Trp Gln Asp Pro Ile Pro Ala Gly Ser Thr Ser Tyr
                435                 440                 445 gat gtc gct gcc gtc aag gct aag atc gct gcc tcc ggc ctt tct gtc      1693
Asp Val Ala Ala Val Lys Ala Lys Ile Ala Ala Ser Gly Leu Ser Val
        450                 455                 460 gcc gat ctg gtt tca acc gca tgg gac agt gcc cgc acc ttc cgt ggt      1741
Ala Asp Leu Val Ser Thr Ala Trp Asp Ser Ala Arg Thr Phe Arg Gly
            465                 470                 475 tcg gac aag cgc ggc ggc gcc aat ggc gcg cgt att cgt ctc gca ccg      1789
Ser Asp Lys Arg Gly Gly Ala Asn Gly Ala Arg Ile Arg Leu Ala Pro
    480                 485                 490 cag aag gat tgg gaa ggc aat gag ccc gcc cgt ctt tcc cgc gtg ctt      1837
Gln Lys Asp Trp Glu Gly Asn Glu Pro Ala Arg Leu Ser Arg Val Leu
495                 500                 505                 510 tcg gtt ctg gag ccg att gcc cgc gaa acc ggt gca agc atc gcc gat      1885
Ser Val Leu Glu Pro Ile Ala Arg Glu Thr Gly Ala Ser Ile Ala Asp
                515                 520                 525 gtg atc gtt ctg gct ggc aat tac ggc gtg gag cag gcg gcg aaa gcg      1933
Val Ile Val Leu Ala Gly Asn Tyr Gly Val Glu Gln Ala Ala Lys Ala
        530                 535                 540 gct ggt ttc gat atc gcc gtg ccc ttc gcg gcc ggt cgt ggt gac gct      1981
```

```
                                                                    -continued Ala Gly Phe Asp Ile Ala Val Pro Phe Ala Ala Gly Arg Gly Asp Ala
        545                 550                 555 tcc gcc gag cag acg gat gcc gac agc ttt gcg ccg ctt gag ccg ctg    2029
Ser Ala Glu Gln Thr Asp Ala Asp Ser Phe Ala Pro Leu Glu Pro Leu
    560                 565                 570 gcg gat ggt ttc cgc aac tgg gtg aag aag gac tat gtc gtc agc ccc    2077
Ala Asp Gly Phe Arg Asn Trp Val Lys Lys Asp Tyr Val Val Ser Pro
575                 580                 585                 590 gaa gag ctg ctg ctc gat cgg gca cag ctt ctt ggc ctc acc gcg ccg    2125
Glu Glu Leu Leu Leu Asp Arg Ala Gln Leu Leu Gly Leu Thr Ala Pro
                595                 600                 605 gaa ctc acc gtc ctc atc ggc ggc ctg cgc gtc atc ggc gcc aat tac    2173
Glu Leu Thr Val Leu Ile Gly Gly Leu Arg Val Ile Gly Ala Asn Tyr
            610                 615                 620 ggc ggt gcg gcg cat ggc gtc ttc acc gat aag ccg ggg gcg ctt aca    2221
Gly Gly Ala Ala His Gly Val Phe Thr Asp Lys Pro Gly Ala Leu Thr
        625                 630                 635 acg gac ttc ttc acg acg ttg acg gac atg gcc tat tcc tgg gtc ccg    2269
Thr Asp Phe Phe Thr Thr Leu Thr Asp Met Ala Tyr Ser Trp Val Pro
    640                 645                 650 acc ggc aac aat ctc tat gag atc cgt gat cgc aag acc ggc gca gcc    2317
Thr Gly Asn Asn Leu Tyr Glu Ile Arg Asp Arg Lys Thr Gly Ala Ala
655                 660                 665                 670 aga tat tcg gca acc cgc gtc gat ctc gtg atc ggc tcc aac tcc atc    2365
Arg Tyr Ser Ala Thr Arg Val Asp Leu Val Ile Gly Ser Asn Ser Ile
                675                 680                 685 ctg cgc gct tat gcg gaa gtt tat gcg cag gac gac aac agg gaa aaa    2413
Leu Arg Ala Tyr Ala Glu Val Tyr Ala Gln Asp Asp Asn Arg Glu Lys
            690                 695                 700 ttc gcc cgc gac ttc att gcc gcc tgg acg aag gtg atg aac gcc gac    2461
Phe Ala Arg Asp Phe Ile Ala Ala Trp Thr Lys Val Met Asn Ala Asp
        705                 710                 715 cgt ttc gat ctg atc tgagcggaag cgattagccg aaaagacaac acctccccga    2516
Arg Phe Asp Leu Ile
        720 gcgatcgggg aggtgttttt gtggcggctt cctctcgatg acggaggccc catattcatt    2576 caacggcggt cggaagacgg aacctgccgc tcgggtgacg acttttcagt tggtccagca    2636 ggcgtcttgc cactcttctc gttttcatgc gcatccgggc cagcgacaat acgccacgg    2696 ccctgttctt cacgcttctt gtcggcgaaa tcgcccgctt cctttttctc gttcatcgtt    2756 ttctcccttc gcgttgtttc gtccttcatt caacgaatga cgaagaggtg ggttccagat    2816 agacaattcc gcagagggcc gaa                                            2839

<210> SEQ ID NO 3
<211> LENGTH: 723
<212> TYPE: PRT
<213> ORGANISM: Agrobacterium tumefaciens

<400> SEQUENCE: 3

Met Asp Ala Thr Ser Lys Pro Ala Gly Lys Cys Pro Val Met His Gly
1               5                   10                  15

Gly Asn Thr Ala Ser Gly Lys Ser Val Thr Glu Trp Trp Pro Asn Ala
            20                  25                  30

Leu Asn Leu Asp Ile Leu His Gln His Asp Thr Lys Thr Asn Pro Leu
        35                  40                  45

Gly Thr Ser Phe Asn Tyr Arg Glu Ala Leu Lys Thr Leu Asp Val Glu
    50                  55                  60
```

```
Ala Leu Lys Ala Asp Leu Arg Ala Leu Met Thr Asp Ser Gln Glu Trp
 65                  70                  75                  80

Trp Pro Ala Asp Trp Gly Ser Tyr Val Gly Met Met Ala Arg Val Thr
                 85                  90                  95

Trp His Ala Ala Gly Ser Tyr Arg Val Thr Asp Gly Arg Gly Gly Ala
            100                 105                 110

Asn Thr Gly Asn Gln Arg Phe Ala Pro Leu Asn Ser Trp Pro Asp Asn
        115                 120                 125

Val Asn Thr Asp Lys Gly Arg Arg Leu Leu Trp Pro Ile Lys Lys Lys
    130                 135                 140

Tyr Gly Asn Lys Ile Ser Trp Ala Asp Leu Ile Ala Leu Ala Gly Thr
145                 150                 155                 160

Ile Ala Tyr Asp Val Ala Gly Leu Lys Thr Phe Gly Phe Ala Phe Gly
                165                 170                 175

Arg Glu Asp Ile Trp Ala Pro Glu Lys Asp Thr Tyr Trp Gly Asp Glu
            180                 185                 190

Lys Glu Trp Leu Ala Pro Ser Asp Gly Arg Tyr Gly Asp Val Ser Lys
        195                 200                 205

Pro Glu Thr Leu Glu Asn Pro Leu Ala Ala Val Gln Met Gly Leu Ile
    210                 215                 220

Tyr Val Asn Pro Glu Gly Val Asn Gly Lys Ser Asp Pro Leu Ala Thr
225                 230                 235                 240

Ala Ala Gln Met Arg Glu Thr Phe Ala Arg Met Gly Met Asp Asp Glu
                245                 250                 255

Glu Thr Val Ala Leu Thr Ala Gly Gly His Thr Ile Gly Lys Ser His
            260                 265                 270

Gly Asn Gly Ser Ala Ala Asn Leu Ser Pro Asp Pro Glu Ala Ala Gly
        275                 280                 285

Pro Glu Tyr Gln Gly Leu Gly Trp Ile Asn Thr Lys Gly Arg Gly Ile
    290                 295                 300

Gly Arg Asp Thr Val Val Ser Gly Ile Glu Gly Ala Trp Thr Ser Glu
305                 310                 315                 320

Pro Thr Lys Trp Asp Asn Gly Phe Phe Asp Met Leu Phe Lys His Glu
                325                 330                 335

Trp Thr Leu Thr His Ser Pro Ala Gly Ala Ser Gln Trp Ala Pro Ile
            340                 345                 350

Thr Ile Ala Glu Glu Asp Lys Pro Val Asp Val Glu Asp Ala Ser Ile
        355                 360                 365

Arg Thr Ile Pro Met Met Thr Asp Ala Asp Met Ala Leu Lys Val Asp
    370                 375                 380

Pro Ile Tyr Arg Glu Ile Ser Leu Lys Phe Lys Asp Asp Gln Asp His
385                 390                 395                 400

Phe Ser Asp Val Phe Ala Arg Ala Trp Phe Lys Leu Thr His Arg Asp
                405                 410                 415

Met Gly Pro Lys Ser Arg Tyr Val Gly Pro Asp Val Pro Ala Glu Asp
            420                 425                 430

Leu Ile Trp Gln Asp Pro Ile Pro Ala Gly Ser Thr Ser Tyr Asp Val
        435                 440                 445

Ala Ala Val Lys Ala Lys Ile Ala Ala Ser Gly Leu Ser Val Ala Asp
    450                 455                 460

Leu Val Ser Thr Ala Trp Asp Ser Ala Arg Thr Phe Arg Gly Ser Asp
465                 470                 475                 480

Lys Arg Gly Gly Ala Asn Gly Ala Arg Ile Arg Leu Ala Pro Gln Lys
```

-continued

```
            485                 490                 495
Asp Trp Glu Gly Asn Glu Pro Ala Arg Leu Ser Arg Val Leu Ser Val
            500                 505                 510

Leu Glu Pro Ile Ala Arg Glu Thr Gly Ala Ser Ile Ala Asp Val Ile
            515                 520                 525

Val Leu Ala Gly Asn Tyr Gly Val Glu Gln Ala Ala Lys Ala Ala Gly
            530                 535                 540

Phe Asp Ile Ala Val Pro Phe Ala Ala Gly Arg Gly Asp Ala Ser Ala
545                 550                 555                 560

Glu Gln Thr Asp Ala Asp Ser Phe Ala Pro Leu Glu Pro Leu Ala Asp
                565                 570                 575

Gly Phe Arg Asn Trp Val Lys Lys Asp Tyr Val Val Ser Pro Glu Glu
                580                 585                 590

Leu Leu Leu Asp Arg Ala Gln Leu Leu Gly Leu Thr Ala Pro Glu Leu
                595                 600                 605

Thr Val Leu Ile Gly Gly Leu Arg Val Ile Gly Ala Asn Tyr Gly Gly
            610                 615                 620

Ala Ala His Gly Val Phe Thr Asp Lys Pro Gly Ala Leu Thr Thr Asp
625                 630                 635                 640

Phe Phe Thr Thr Leu Thr Asp Met Ala Tyr Ser Trp Val Pro Thr Gly
                645                 650                 655

Asn Asn Leu Tyr Glu Ile Arg Asp Arg Lys Thr Gly Ala Ala Arg Tyr
                660                 665                 670

Ser Ala Thr Arg Val Asp Leu Val Ile Gly Ser Asn Ser Ile Leu Arg
            675                 680                 685

Ala Tyr Ala Glu Val Tyr Ala Gln Asp Asp Asn Arg Glu Lys Phe Ala
            690                 695                 700

Arg Asp Phe Ile Ala Ala Trp Thr Lys Val Met Asn Ala Asp Arg Phe
705                 710                 715                 720

Asp Leu Ile

<210> SEQ ID NO 4
<211> LENGTH: 28
<212> TYPE: DNA
<213> ORGANISM: Agrobacterium tumefaciens

<400> SEQUENCE: 4
ggtgcgctag ccaaattcgt caccaagc                                      28

<210> SEQ ID NO 5
<211> LENGTH: 24
<212> TYPE: DNA
<213> ORGANISM: Agrobacterium tumefaciens

<400> SEQUENCE: 5
caatcgctag cgttcggccc tctg                                          24
```

METHODS AND KITS FOR IDENTIFYING SCAVENGERS OF REACTIVE OXYGEN SPECIES (ROS)

REFERENCE TO RELATED APPLICATIONS

This is the U.S. National Stage of International Application No. PCT/SG02/00018, filed Feb. 5, 2002 (published in English under PCT Article 21(2)), which in turn claims the benefit of U.S. Provisional Patent Application No. 60/266,657, filed Feb. 5, 2001. Both applications are incorporated herein in their entirety.

FIELD OF INVENTION

This invention relates to methods of identifying, and/or determining the ROS-scavenging ability of, a compound with ROS-scavenging function.

BACKGROUND OF THE INVENTION

Aerobic metabolism in living organisms can lead to generation of reactive oxygen species (ROS), which include hydroxyl radicals, superoxide anion, hydrogen peroxide and nitric oxide. Production of ROS can be due to various enzymatic and non-enzymatic processes. In aerobic organisms, ROS are formed from the partial reduction of molecular oxygen to water during oxidative metabolism. Bacterial cells produce endogenous hydrogen peroxide from the dismutation of superoxide or hydroxyl radical as a product of the respiratory chain when oxygen is used as the terminal electron acceptor. Enteric bacteria (e.g. *Salmonella typhimurium* and *E. coli*) encounter toxic levels of hydrogen peroxide produced by macrophages during engulfment.

Under normal conditions, ROS may play an important role in different biological processes. However, when ROS are excessively produced under certain unusual conditions, they can cause oxidative damage to DNA, proteins and lipids.

ROS have been implicated in the pathogenesis of many different disease situations as well as harmful conditions. These include aging, AIDS, atherosclerosis, cancer, cataracts, congestive heart failure, diabetes, inflammatory disorders, rheumatoid arthritis, and neuro-degenerative diseases such as Alzheimer's, Parkinson's, multiple sclerosis, and Down's syndrome, in addition to exposure to pollutants and ionizing irradiation.

Living organisms have developed different ways of coping with the ROS. The capacity of enzymatic or non-enzymatic antioxidants to quench the ROS can help cells to defend against the oxidative stress. Therefore, antioxidants have been linked to and used for disease prevention.

Antioxidants may be proteins, such as ferritin, lactoferritin and transferritin, or enzymes, such as superoxide dismutase, catalase and glutathione peroxidase. Nonenzymatic antioxidants may be macromolecules, such as albumin, copper-binding ceruloplasmin and hemoglobin, or small molecules which may be water-soluble antioxidants, such as vitamin C, uric acid and bilirubin or lipid-soluble antioxidants, such as vitamin E, carotenoids, retinoids and ubiquinol-10.

However, these natural defenses can be overwhelmed in many pathological states. More potent antioxidants should be supplemented to deal with the oxidative stresses. Screening and assay methods are needed to identify potent antioxidants; but the current methods are both time-consuming and expensive. In addition, they cannot measure the intracellular antioxidant activities, which are more relevant to biological applications. Therefore, a simple method that can measure the intracellular antioxidant activities and hence can be used to search for better oxidant scavenging molecules is of great importance in the pharmaceutical and nutraceutical fields.

The public has shown an increasing interest in the natural antioxidants contained in dietary supplements, as antioxidants can give health benefits by preventing oxidative damage caused by ROS. Standardized assays to assess antioxidant activities and distinguish different antioxidants are useful. Such assay methods are useful to properly assess and label antioxidant products. Such assays are also useful for measuring activities of antioxidants for use as food supplements, natural products and drugs.

Farr (U.S. Pat. Nos. 5,585,252, 5,811,231 and 5,589,337) have described use of stress promoters fused to reporter genes to determine toxicity.

Catalase is a protein antioxidant. Catalases catalyze the dismutation of hydrogen peroxide to water and oxygen. The primary role for catalases is to protect the cells against the damage caused by reactive oxygen species to cellular components, including nucleic acids, proteins and cell membranes. Catalases have been implicated to be important for the survival of some pathogenic bacteria during infection and even for the life span of a multi-cellular organism.

*Agrobacterium tumefaciens* is a soil-borne plant pathogen that causes crown gall tumors on many plant species. A chromosomal gene katA encoding a catalase has been identified that is involved in detoxification of $H_2O_2$ released during *Agrobacterium*-plant interaction (Xu and Pan, 2000).

SUMMARY OF THE INVENTION

The present invention relates to a method for determining the ability of a compound to remove an ROS. The method generally comprises: a) providing a cell containing an ROS-inducible promoter (RIP) which drives expression of a reporter gene. The reporter gene is heterologous to the promoter to which it is operably linked. b) exposing the cell to a compound potentially able to remove the ROS. c) measuring a change in the ROS-inducible expression level of the reporter gene in the cell when the cell is exposed to the compound. A reduction in the reporter protein level would indicate that the compound is able to remove the ROS.

The invention further relates to a method for selecting a nucleic acid which encodes a protein-potentially able to remove an ROS. The method generally comprises: a) Providing cells containing an ROS-induced promoter which drives expression of a reporter gene. The reporter gene is heterologous to the promoter to which it is operably linked. b) Introducing into the cells expression vectors containing different nucleic acids, such as those found in a cDNA library, or in a library where the nucleic acids have been mutagenized. These nucleic acids encode proteins which are potentially able to remove the ROS. c) Measuring a change in the ROS-inducible expression of the reporter gene in the cells when the nucleic acids are expressed. d) Selecting for cells with reduced ROS-inducible expression of the reporter gene. e) Isolating the nucleic acid from the cells with reduced ROS-inducible expression of the reporter gene. The nucleic acid isolated by such a procedure likely encodes a protein able to remove the ROS.

In one embodiment, the different nucleic acids all encode proteins able to remove ROS. By selecting for cells with the greatest degree of reduction in the level of reporter protein, the most efficient ROS remover may be identified.

The method of the invention does not require that the cell be exposed to an external source of ROS. Rather, the ROS which induces the ROS-inducible promoter may be intracellular. In one embodiment, the intracellular level of the ROS may be elevated by methods known in the art. The intracellular level of ROS such as $H_2O_2$ may also be induced by acid pH, especially in bacteria such as *A. tumefaciens*. In another embodiment, the intracellular level of the ROS may be made constitutively elevated by using a cell which has been genetically modified.

Cells containing such genetic modifications are known in the art and may have, for example, modified genes of the respiratory chain so that the redox balance of the cell is disturbed. Other genetic modifications may involve knocking out functional enzymes which break down or remove ROS intracellularly, such as catalase, superoxide dismutase, alkyl hydroperoxidase, and glutathione reductase.

As is clear from above, the method of the invention also does not require that the potential ROS-removing compound be exposed to the cell extracellularly. Rather, the compound, in this case a gene product, may be expressed from a nucleic acid inside the cell.

In a preferred embodiment, the cell expressing the RIP-reporter does not express the functional native gene product, i.e. that which is naturally expressed from the promoter to which the reporter gene is operably linked. Absence of the native gene function ensures that no complicating mechanism such as a feedback loop interferes with the correlation between the ability of a compound to remove an ROS and the RIP-reporter expression level.

In one embodiment, the ROS-inducible promoter is from a gene selected from the group consisting of: AhpCF, Bcp, Dps, gor, KatA, KatB/AnkB, KatG, TrxB, human MAP kinase phosphatase 1 (MKP-1) genes; mammalian hic-5 genes, the isc operon; *Escherichia coli* zwf, fpr, fumC, micF, nfo, and sodA genes; *Azotobacter vinelandii* spr gene; *Xanthomonas oryzae* pv *oryzae* katX gene; rat and human haem oxygenase-1 (HO-1); yeast 2-deoxyglucose-6-phophate phosphatase (DOG2); catalase; human manganese superoxide dismutase (MnSOD); rat glutathione S-transferase (GST); human interstitial collagenase (MMP-1); human glutathione peroxidase (GPX2); fish metallothionein (MT); and rat multidrug resistance type 1 (mdr1).

In another embodiment, the ROS is $H_2O_2$. Where it is desirable to identify or select for $H_2O_2$-removing compounds, an $H_2O_2$-inducible promoter is used. Such a promoter may be from the following genes: AhpCF, Bcp, Dps, gor, KatA, KatB/AnkB, KatG, TrxB, human MAP kinase phosphatase 1 (MKP-1) genes; mammalian hic-5 genes, and the isc operon.

In another embodiment, the cell used in the methods described above is a bacterial cell. It is understood that if a bacterial cell is used, the ROS-responsive promoter must function as such in bacteria and the reporter gene must encode a protein functional in bacteria. Likewise, if a plant cell, a yeast cell, or a mammalian cell is used, the ROS-responsive promoter and the reporter protein must be functional in the particular chosen cell type.

The present invention also relates to diagnostic kits for determining the ability of a gene product to remove an ROS. Such a kit generally comprises: a) a cell which contains an ROS-inducible promoter driving expressing of a reporter gene. The reporter gene is understood to be heterologous to the promoter to which it is operably linked. b) means for introducing in the cell a nucleic acid encoding a gene product; and (c) instructions for determining a reduction in ROS-inducible expression of the reporter gene in the cell once the nucleic acid is expressed. This would indicate whether the gene product is able to remove the ROS.

The kit of the invention provides components for carrying out the methods of the invention. Accordingly, in one embodiment, the kit further contains means for measuring the level of the product of the reporter gene. The kit may further comprise means for elevating the intracellular level of the ROS in the cell. The cell provided in the kit may be genetically modified to contain an elevated intracellular level of an ROS, or may lack at least one naturally occurring ROS-removing activity. The cell of the kit may also lack a gene encoding an active enzyme such as catalase, superoxide dismutase, alkyl hydroperoxidase, and glutathione reductase.

The ROS-inducible promoter contained in the kit may be from a gene such as AhpCF, Bcp, Dps, gor, KatA, KatB/AnkB, KatG, TrxB, human MAP kinase phosphatase 1 (MKP-1) genes; mammalian hic-5 genes, the bacterial isc operon; *Escherichia coli* zwf, fpr, fumC, micF, nfo, soi28, and sodA genes; *Azotobacter vinelandii* spr gene; *Xanthomonas oryzae* pv *oryzae* katX gene; rat and human haem oxygenase-1 (HO-1); yeast 2-deoxyglucose-6-phophate phosphatase (DOG2); catalase; human manganese superoxide dismutase (MnSOD); rat glutathione S-transferase (GST); human interstitial collagenase (MMP-1); human glutathione peroxidase (GPX2); fish metallothionein (MT); and rat multidrug resistance type 1 (mdr1).

In one embodiment, the kit is used to determine the ability of a certain compound to remove $H_2O_2$. Preferably, the kit provides an $H_2O_2$-inducible promoter from a gene such as AhpCF, Bcp, Dps, gor, KatA, KatB/AnkB, KatG, TrxB, human MAP kinase phosphatase 1 (MKP-1) genes; mammalian hic-5 genes, and the isc operon.

In another embodiment the cell provided by the kit is a bacterial cell and the reporter gene encodes a protein functional in bacteria. In a preferred embodiment, the bacterial cell is *Agrobacterium tumefaciens*.

In preferred embodiments of the method or kit of the invention, the ROS-inducible promoter is from the KatA gene of *Agrobacterium tumefaciens*.

BRIEF DESCRIPTION OF THE DRAWINGS

FIG. 1. Alignment of the amino acid sequence of the *Agrobacterium tumefaciens* katA gene product with the homologous catalase sequences. Alignment was completed by using the DNAsis program. Atu KatA represents the *A. tumefaciens* katA gene product; Lpn KatB represents the *Legionella pneumophila* katB gene product; Bst Cat represents the *Bacillus stearothermophilus* catalase.

DETAILED DESCRIPTION OF THE EMBODIMENTS

Figure 2:
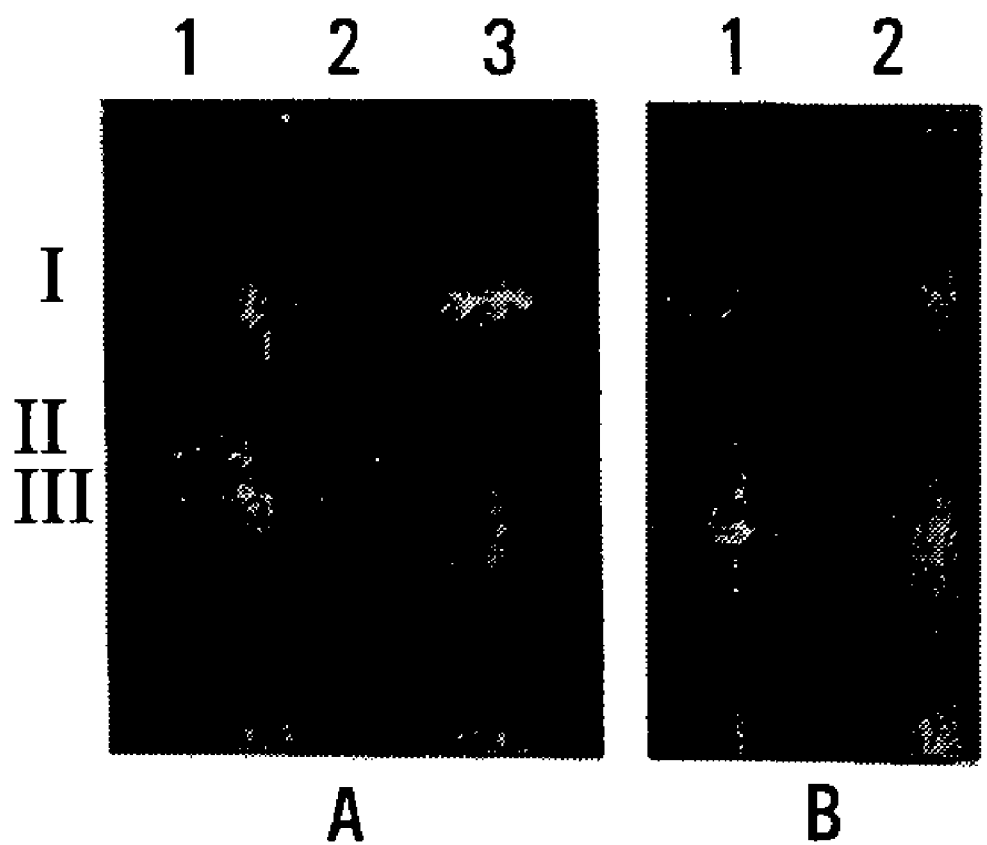
FIG. 2. Catalase isozyme assays. A. *Agrobacterium tumefaciens* strains A348 (lane 1), AG6 (pXQ9) (lane 2) and AG6 (lane 3) were grown overnight at 28° C. in MG/L liquid medium. Crude cell extracts were prepared as described in the Materials and Methods. For each strain, 20 µl of crude cell extract was loaded and electrophoresed on 7.5% nondenaturing gel. B. 40 µl (lane 1) and 20 µl (lane 2) of A348 cell crude extract (that had been diluted 2× further after the dilution described in the Materials and Methods) was loaded and electrophoresed. Catalase isozymes were visualised by activity staining according to Clare et al. (1984).

To determine whether a compound is able to remove an ROS, an ROS-inducible promoter (RIP) is fused to a reporter gene to drive its expression. The reporter gene is heterologous to the promoter to which it is operably linked. The RIP-reporter construct is then stably transformed into the cell. To test whether a certain compound is an ROS-remover, the cell is exposed to the test compound. Preferably, the cell is exposed to the test compound intracellularly. If necessary, the intracellular level of the ROS is induced, and the ROS-inducible expression level of the reporter gene in the cell is measured. A reduction in the reporter protein level when the cell is exposed to the compound would indicate that the compound is able to remove the ROS.

The test compound may also be provided by being expressed in a neighbouring cell, rather than being expressed from the cell containing the RIP.

As used herein, the terms "reactive oxygen species" (ROS) and "oxidants" are used interchangeably, and include hydroxyl radicals, superoxide anion, hydrogen peroxide and nitric oxide.

ROS-removing compounds are anti-oxidants or oxidant scavengers. Namely, these compounds have the ability remove ROS by breaking them down chemically, or by sequestering them away from solution. Known ROS-removing compounds include proteins, such as ferritin, lactoferritin and transferritin, or enzymes, such as superoxide dismutase, catalase and glutathione peroxidase. Nonenzymatic antioxidants may be macromolecules, such as albumin, copper-binding ceruloplasmin and hemoglobin, or small molecules such as water-soluble antioxidants (e.g. vitamin C, uric acid and bilirubin) or lipid-soluble antioxidants (e.g. vitamin E, carotenoids, retinoids and ubiquinol-10).

In a preferred embodiment, the test compounds with potential ROS-removing capability are proteins expressed intracellularly. They are often proteins heterologous to the cells containing the RIP-reporter construct. However, a polypeptide naturally present in such cells may also be tested as a ROS-removing compound provided that the gene encoding the functional polypeptide has been knocked out from the cell.

The term "heterologous" means, in the context of the present invention, that the components are not found naturally together. For example, a reporter gene which is heterologous to the promoter to which it is linked is not the natural coding sequence of the gene from which the promoter is derived.

The term "vector" refers to a nucleic acid sequence that is capable of propagating in particular host cells and can accommodate inserts of foreign nucleic acid. Typically, vectors can be manipulated in vitro to insert foreign nucleic acids and the vectors can be introduced into host cells such that the inserted nucleic acid is transiently or stably present in the host cells.

The term "expression vector" refers to a vector designed to express inserted nucleic acid sequences. Such vectors may contain a powerful promoter located upstream of the insertion site.

The term "expression" in the context of nucleic acids refers to transcription and/or translation of nucleic acids into mRNA and/or protein products.

The term "expression library" refers to a library of nucleic acid fragments contained as inserts in an expression vector.

The term "stable transformation" refers to the continued presence of a nucleic acid sequence in a host cell for a period of time that is at least as long as that required to carry out the methods of the present invention. Stable transformation can be achieved through integration of the construct into a host cell chromosome, or engineering the construct so that it possesses elements that ensure its continued replication and segregation within the host (i.e., an artificial chromosome), or alternatively, the construct may contain a selectable marker (e.g., a drug resistance gene) so that persistence of the construct in the cell is ensured by growing the host cells under selective conditions (e.g., in drug-containing media).

The term "cell" or "host cell" in the present invention refers to a cell of prokaryotic or eukaryotic origin that can serve as a recipient of an introduced vector. The host cell often allows replication and segregation of the vector that resides within. In certain cases, however, replication and/or segregation are irrelevant; expression of vector or insert DNA is the objective. Typical bacterial host cells include *E. coli, B. subtilis* and *A. tumefaciens;* fungal host cells include *S. cerevisiae* and *S. pombe*; plant cells include those isolated from *A. thaliana,* and *Z. maize*; insect host cells include those isolated from *D. melanogaster, A. aegypti,* and *S. frugiperda*; and mammalian cells include those isolated from human tissues and cancers including melanocyte (melanoma), colon (carcinoma), prostate (carcinoma), brain (glioma, neuroblastoma, astrocytoma) and liver (hepatoma).

An ROS-inducible promoter is one which, in response to the presence of the ROS inside the cell, expression from the promoter is increased. Numerous ROS-inducible promoters are known in the art. They include: AhpCF, Bcp, Dps, gor, KatA, KatB/AnkB, KatG, TrxB, human MAP kinase phosphatase 1 (MKP-1) genes; mammalian hic-5 genes, the isc operon; *Escherichia coli* zwf, fpr, fumC, micF, nfo, and sodA genes; *Azotobacter vinelandii* spr gene; *Xanthomonas oryzae* pv *oryzae* katX gene; rat and human haem oxygenase-1 (HO-1); yeast 2-deoxyglucose-6-phophate phosphatase (DOG2); catalase; human manganese superoxide dismutase (Mn-SOD); rat glutathione S-transferase (GST); human interstitial collagenase (MMP-1); human glutathione peroxidase (GPX2); fish metallothionein (MT); and rat multidrug resistance type 1 (mdr1).

It is expected that most of the promoters above would be functional to some degree in a heterologous cell type. However, it is preferred that promoters naturally found in bacteria would be used in bacteria, and yeast promoter in yeast cells, and mammalian promoters in mammalian cells, according to the methods of the invention.

In a preferred embodiment, the ROS is $H_2O_2$, and the $H_2O_2$-inducible promoter is from a gene such as AhpCF, Bcp, Dps, gor, KatA, KatB/AnkB, KatG, TrxB, human MAP kinase phosphatase 1 (MKP-1) genes; mammalian hic-5 genes, and the isc operon.

The RIP-reporter vector is customized so that reporter expression reflects as closely as possible the ROS level of the host cell. Thus, the expression vector is designed so that the reporter gene is placed under control of ROS-response cis regulatory elements functional in the host cell. Preferably, the reporter is expressed at a low level in the absence of the ROS; i.e. the basal activity of the promoter should be low so that induction by ROS is readily detectable.

A partial listing of the genes, their organism of origin, and Genbank accession numbers are provided below. A brief description of some of these genes and reference publications are also provided:

*Streptococcus mutans* ahpC and nox1 genes for alkyl hydroperoxidase and NADH oxidase/alkyl hydroperoxidase reductase, ACCESSION AB010712.

*Mycobacterium marinum* alkylhydroperoxide reductase (ahpC) gene, ACCESSION AF034861.

*Bacteroides fragilis* alkyl hydroperoxide reductase subunit C (ahpC) and alkyl hydroperoxide reductase subunit F (ahpF) genes, ACCESSION AF129406.

*Salmonella typhimurium* alkyl hydroperoxide reductase (ahpC) and (ahpF) genes, ACCESSION J05478.

*Mycobacterium avium* alkyl hydroperoxidase C (ahpC) gene, ACCESSION U18263.

*Mycobacterium tuberculosis* alkyl hydroperoxidase C (ahpC) gene, ACCESSION U18264.

*Mycobacterium smegmatis* alkyl hydroperoxide reductase C (ahpC) gene, ACCESSION U43719.

*Mycobacterium intracellulare* alkyl hydroperoxidase C (ahpC), ACCESSION U71061.

*Staphylococcus aureus* alkyl hydroperoxide reductase subunit C (aphC) and subunit F (aphF) genes, ACCESSION U92441 X85029.

*Escherichia coli* bacterioferritin comigratory protein (bcp), ACCESSION M63654 M37689.

*Escherichia coli* DNA binding protein Dps (dps) gene, ACCESSION AF140030.

*Bacteroides fragilis* non-specific DNA-binding protein Dps (dps), ACCESSION AF206033.

*Synechococcus sp.* nutrient-stress induced DNA binding protein (dpsA) gene, ACCESSION U19762.

*Streptococcus thermophilus* glutathione reductase (gor) gene, ACCESSION L27672.

*E.coli* gor gene encoding glutathione reductase, ACCESSION M13141.

*P. aeruginosa* gor gene for glutathione reductase (EC 1.6.4.2), ACCESSION X54201.

*Agrobacterium tumefaciens* catalase (KatA), SEQ ID NO:1.

*Vibrio fischeri* catalase (katA) gene, ACCESSION AF011784.

*Pseudomonas aeruginosa* catalase isozyme A (katA) gene, ACCESSION AF047025.

*Actinobacillus actinomycetemcomitans* catalase (katA) gene, ACCESSION AF162654.

*Legionella pneumophila* catalase-peroxidase (katA) gene, ACCESSION AF276752.

*Staphylococcus aureus* catalase gene, strain ATCC12600. ACCESSION AJ000472.
*Lactobacillus sake* catalase (katA) gene, ACCESSION M84015.
*Rhizobium meliloti* catalase (katA) gene, ACCESSION U59271.
*Pseudomonas fluorescens* plasmid pAM10.6 catalase isozyme (katA) ACCESSION U72068.
*H.pylori* katA gene, ACCESSION Z70679.
*B.subtilis* 25 kb genomic DNA segment (from sspE to katA), ACCESSION Z82044.
*Pseudomonas aeruginosa* paraquat inducible catalase isozyme B (katB), ankyrin (ankB), ACCESSION U89384.
*Caulobacter crescentus* catalase-peroxidase (katG) gene, ACCESSION AF027168.
*Mycobacterium smegmatis* catalase-peroxidase (katG) gene, ACCESSION AF196484.
Synechococcus PCC6301 catalase-peroxidase gene, ACCESSION AF197161.
*Mycobacterium leprae* DNA for catalase-peroxidase, ACCESSION D89336.
*E.coli* katG gene encoding catalase HP1, ACCESSION M21516.
*Salmonella typhimurium* Kat G gene for hydroperoxidase I. ACCESSION X53001.
*M.tuberculosis* katG gene for catalase-peroxidase. ACCESSION X68081 S42739.
*M.bovis* katG gene. ACCESSION X83277.
*M.smegmatis* katG gene. ACCESSION X98718.
*M.fortuitum* katGI gene. ACCESSION Y07865.
*M.fortuitum* katGII gene. ACCESSION Y07866.
*Mycobacterium smegmatis* thioredoxin reductase (trxB) and thioredoxin (trxA) genes, ACCESSION AF023161.
*Streptomyces coelicolor* sigT, trxB and trxA genes, ACCESSION AJ007313.
*Clostridium litorale* thioredoxin reductase (trxB), and thioredoxin (trxA) genes, ACCESSION U24268.
*Mycoplasma pneumoniae* thioredoxin reductase K04_orf315 (trxB) gene, ACCESSION U51988.
The sodA gene encodes superoxide dismutase and is strongly induced when cells are exposed to chemicals that produce superoxide radicals in the cell, such as paraquat, plumbagin, menadione, streptonigrin, methylene blue and phenazine methyl sulfate. SodA gene induction depends upon an increase in steady state superoxide concentration, not necessarily upon cellular damage caused by superoxides.
The soi28 gene encodes a pyruvate:flavodoxin oxidoreductase. This gene is induced by superoxide-producing reagents only. Specifically, the soi28 gene is induced when two small, thiol-containing proteins, flavodoxin and ferredoxin, become oxidized.
The ahp gene is induced by hydrogen peroxide and organic hydroperoxides, both exogenous and those formed upon peroxidation of proteins and fatty acids.
soi17 and soi19 respond to superoxides [T. Kogoma et al., (1988)].
zwf encodes glucose-6-hydrogenase and is induced by superoxide-producing compounds and nitric oxide [Greenberg et al.(1990)].
micF encodes antisense RNA that shuts off translation of the porin gene, ompF and is induced by superoxides [Greenberg et al.(1990)].
The nfo gene encodes a DNA repair enzyme and is specifically induced by redox active agents, such as paraquat and menadione [Farr et al.(1991)].

If the nucleotide sequence of the ROS-inducible gene is known, polymerase chain reaction may be used to produce fusions with the promoter. Specifically, primers are synthesized which are complementary to the 5' and 3' ends of the ROS- inducible promoter portion of the gene, hybridizes those primers to denatured, total DNA under appropriate conditions and performs PCR. In this manner, clonable quantities of any sequenced promoter may be obtained. Once the promoter DNA has been obtained, it is ligated to a DNA encoding the reporter gene in an appropriate vector, such as pRS415 for *E. coli*, which contains a multiple cloning site just upstream from the lacZ gene. Numerous vectors for expressing reporter genes are known in the art or are commercially available. The methods are well-known in the art.

A reporter gene as used in the present invention essentially encodes any gene product that can be expressed in the cell of interest and is assayable and detectable. The reporter gene must be sufficiently characterized such that it can be operably linked to the promoter. Reporter genes used in the art include the LacZ gene from *E. coli* (Shapiro S. K., Chou J., et al., Gene November; 25: 71-82 (1983)), the CAT gene from bacteria (Thiel G., Petersohn D., and Schoch S., Gene February 12; 168: 173-176 (1996)), the luciferase gene from firefly (Gould S. J., and Subramani S., 1988), the GFP gene from jellyfish (Chalfie M. and Prashner D. C., U.S. Pat. No. 5,491,084), galactose kinase (encoded by the galK gene), and beta-glucosidase (encoded by the gus gene). These have been primarily used to monitor expression of genes in the cytoplasm. To monitor expression at the cell surface, a labeled antibody that binds to the cell surface marker (e.g., CD20) may be used to quantify the level of reporter (Koh J., Enders G. H., et al, 1995).

Of these reporters, autofluorescent proteins (e.g., GFP) and the cell surface reporters are preferred for use in monitoring living cells, because they act as "vital dyes". Their expression can be evaluated in living cells, and the cells can be recovered intact for subsequent analysis. Vital dyes, however, are not specifically required by the methods of the present invention. It is also very useful to employ reporters whose expression can be quantified rapidly and with high sensitivity. Thus, fluorescent reporters (or reporters that can be labeled directly or indirectly with a fluorophore) are especially preferred. This trait permits high throughput screening on a flow sorter machine such as a fluorescence activated cell sorter (FACS).

GFP is a member of a family of naturally occurring fluorescent proteins, whose fluorescence is primarily in the green region of the spectrum. GFP has been developed extensively for use as a reporter and several mutant forms of the protein have been characterized that have altered spectral properties. High levels of GFP expression have been obtained in cells ranging from yeast to human cells. It is a robust, all-purpose reporter, whose expression in the cytoplasm can be measured quantitatively using a flow sorter instrument such as a FACS.

The diagnostic kits and methods of this invention rely on the induction of specific ROS-inducible promoters to alter expression of the reporter gene. This change in expression level is measured both qualitatively and quantitatively. In order to be useful in those kits and methods, the particular stress promoter must be operably linked to the gene which encodes the reporter product.

The term "operable linkage" refers to the positioning of the promoter relative to the gene encoding the reporter product such that transcription of the gene is regulated by the promoter. Such positioning is well known in the art and involves positioning the promoter upstream (5') of the gene so that transcription is not impeded by extraneous termination signals and where the spacing between the promoter initiation site and the regulatory sequences of the promoter are optimal for transcription.

Also within the scope of this invention are constructs wherein the reporter product is in fusion with the N-terminal portion of the native gene product, i.e. the gene product of the promoter to which the reporter is fused. It is important that the portion of native gene product fused to the reporter does not retain the function of the full length native gene product.

The choice of bacterial strain to express the particular RIP-reporter construct and thus useful in the methods and kits of this invention is only limited by the strain's ability to produce the functional reporter and its inability to synthesize the reporter in its untransformed state. Most preferably, the strain used should be defective in genes which endogenously remove ROS intracellularly. Such genes include those encoding catalase, superoxide dismutase, alkyl hydroperoxidase, and glutathione reductase. For example, where an $H_2O_2$-inducible promoter is used, it is preferred that the endogenous catalase genes be knocked out or mutated in the cells so that the cells lose or have decreased capacity to break down $H_2O_2$ endogenously.

Eukaryotic cells useful in the methods and kits of the invention include cell lines established from primary tissue, as well as those cell lines and cultures available from the American Type Culture Collection (ATCC, Rockville, Md.).

The method and kits of the invention rely on a detectable reduction in ROS-inducible reporter expression to test whether a compound is capable of removing ROS. This requires that the level of reporter expression be sufficiently high in the absence of an ROS-removing compound, so that a reduction is detectable. In some embodiments, the method involves elevating the intracellular level of the ROS. Methods used to elevate the concentration of various intracellular ROS are known.

In bacteria, intracellular levels of $H_2O_2$ may be elevated by using glucose/glucose oxidase (GOX) or reduced glutathione (GSH) as $H_2O_2$-generating systems (Saliim et al. 2001). In *Agrobacterium*, intracellular levels of $H_2O_2$ may be elevated by acid conditions. In mammalian cells and in yeast, depletion of intracellular glutathione raises intracellular ROS. In at least mammalian cells, glutathione may be depleted by application of buthionine sulfoximine. Insuline stimulation also generates a burst of intracellular $H_2O_2$ in insulin-sensitive hepatoma and adipose cells (Mahadev et al. 2001). In Arabidopsis, application of dexamethasone activates MAP kinases and results in the generation of $H_2O_2$ (Ren et al. 2002).

In other embodiments, the method involves using cells where the cells have been genetically modified so that there is an elevated intracellular level of an ROS. In bacteria, *E. coli* strains where modulation of expression of superoxide dismutase results in modulation of intracellular superoxide (Gort and Imlay, 1998). In yeast, expression of cytochrome peroxidase, superoxide dismutase or the GSH1 gene may be modulated. In fibroblasts, cells that stably express Nox1 produces a marked increase in intracellular $H_2O_2$, as well as some increase in superoxide level (Arnold et al. 2001).

In an exemplary embodiment, an assay testing for a compound for its ability remove $H_2O_2$ would proceed along the following line. An expression construct which expresses a potential $H_2O_2$-remover is introduced into a cell line which contains a reporter gene under control of an $H_2O_2$-inducible promoter, such as the *A. tumefaciens* strain AG6. Production of intracellular $H_2O_2$ may be induced, for example by exposing the cells to low pH medium. The level of reporter protein, as indicated by the level of fluorescence if the reporter is GFP, would be reduced in the cells expressing an $H_2O_2$-removing compound, compared to the control cells in which the compound is absent.

An aspect of the invention relates to a method for selecting a nucleic acid which encodes a protein potentially able to remove an ROS. In this method, cells are provided which contain the RIP-reporter gene construct as described above. Expression vectors containing different nucleic acids, such as those found in a cDNA library, or in a library where the nucleic acids have been mutagenized, are used to transform the cells. These nucleic acids encode proteins which are potentially able to remove the ROS. Any reduction in the ROS-inducible expression of the reporter gene is measured, as described above, when the nucleic acids are expressed. The cells with reduced ROS-inducible expression of the reporter gene are then selected and the nucleic acid used to transform the cell is isolated. This nucleic acid would likely encode an ROS-removing protein.

The term "library" refers to a collection of nucleic acid fragments that may individually range in size from about a few base pairs to about a million base pairs. These fragments are contained as inserts in vectors capable of propagating in certain host cells such as bacterial, fungal, plant, insect, or mammalian cells.

The term "plurality of nucleic acids" refers to a set of nucleic acid molecules from any source. For example, a plurality of nucleic acids may comprise total genomic DNA, genomic DNA from one or more chromosomes, cDNA that has been reverse-transcribed from total cellular RNA or from messenger RNA (mRNA), total cellular RNA, mRNA, or a set of nucleic acid molecules synthesized in vitro either individually, or using combinatorial methods. Plurality of nucleic acids is understood to include, e.g. an expression library.

The terms "bright" and "dim" in the context of a cell sorter refer to the intensity levels of fluorescence (or other modes of light emission) exhibited by particular cells: Bright cells have high intensity emission relative to the bulk population of cells, and by inference, high levels of reporter gene expression; dim cells have low intensity emission relative to the bulk population.

The term "flow sorter" refers to a machine that analyzes light emission intensity from cells or other objects and separates these cells or objects according to parameters such as light emission intensity.

In one embodiment, the method using GFP as a reporter protein, to select for ROS-removing proteins is as follows. The ROS-inducible promoter-GFP expression construct is introduced into the chosen host cells and a stable expresser is selected. This GFP-expressing line is clonally expanded to generate a population that is bright green. A library encoding potential ROS-removers is introduced into the host cells to generate a population of GFP-containing cells, some of which also express ROS-removers. This population is examined using a flow sorter device and cells are sorted into two populations: cells that continue to express GFP at levels similar to the cells before introduction of the library inserts.; and, cells that express reduced levels of GFP. The inserts encoding ROS-removers from such "dim" cells are isolated and either used to determine their DNA sequences, or reintroduced into the GFP-containing host cells for another cycle of selection and enrichment.

One can envision a flow sorter profile diagram of the selection procedure described above. The fluorescence intensity of a population of host cells containing the library inserts prior to selection would have a normal distribution. This presorted population is used to select cells on the left tail of the distribution. The dim cells on the left of the distribution are selected and inserts from these cells are reintroduced into the original host cells. The fluorescence intensity distribution that ensues from cells transformed with such a sub-library of sequences would become skewed to the left (i.e., the mean fluorescence intensity decreases).

The present invention may use a flow sorter such as a FACS or equivalent device to screen through large numbers of host cells containing expression library inserts encoding potential ROS-removing proteins, to identify those that can remove ROS; namely, cells that have reduced levels of reporter molecule expression. Host cells which have an elevated level of ROS and which have the reporter (e.g., GFP) present under control of the ROS-inducible promoter will have a constitutively high level of reporter expression. When the expression library inserts are expressed in these cells, the large majority of cells that are analyzed by FACS are expected to have retained this high level. However, a small number may exhibit reduced expression, detected on the FACS as cells that fall on the dimmer side of the cell fluorescence distribution. These dim cells can be collected and grown in isolation of the others. Such a procedure results in enrichment from the starting population of cells for those that contain ROS-removers, which effectively reduce the level of inducer ROS, thereby reducing the level of reporter expression. These selected, dim cells can be used to reisolate the perturbagen fragments by, e.g., PCR using primer sites that flank the library inserts, so as to build a sub-library of library inserts enriched for those that cause reduced reporter expression. The sub-library of fragments can be recloned (using e.g., the same expression vector) and reintroduced into the host cells, and the screening/selection process can be repeated as many times as necessary.

After a sufficient number of cycles, a substantial difference should be observed in the fluorescence intensity distribution of the original reporter-containing host cells as compared to the host cells harboring the enriched ROS-removing sub-library inserts. Preferably, the procedure should be repeated until a minimal overlap is observed between these two fluorescence intensity distributions. Ultimately, the process of FACS sorting and cycling should result in a population of nucleic acids encoding ROS-removers that inhibit expression of the reporter. These can be isolated and studied individually by molecular cloning and DNA sequence analysis.

In order that the invention described herein may be more fully understood, the following examples are set forth. It should be understood that these examples are for illustrative purposes only and are not to be construed as limiting this invention in any manner.

EXAMPLE 1

Materials, Techniques and Assay Conditions

Strains, plasmids, and growth conditions: The strains and plasmids used in this study are listed and described in Table 1. *Agrobacterium tumefaciens* strains were grown in MG/L, IB or AB medium (Cangelosi et al., 1991) at 28° C., supplemented with 100 µg/ml kanamycin, 5 µg/ml tetracycline, or 100 µg/ml carbenicillin as required. *Escherichia coli* strains were grown on Luria-Bertani (LB) medium (Sambrook et al., 1989) at 37° C., supplemented with 50 µg/ml kanamycin, 10 µg/ml tetracycline, or 50 µg/ml ampicillin as required. Mini-Tn5 transposon mutagenesis of *A. tumefaciens* strain A348 was carried out by pAG408 as described (Suarez et al., 1997).

Southern analysis: Total DNA was extracted as described previously (Charles and Nester, 1993) from the *A. tumefaciens* mutant AG6. Approximately 1 µg of total DNA was digested with ClaI or NruI and then electrophoresed on a 0.9% agarose gel. The DNA fragments were then transferred onto nylon membrane Zeta-Probe GT (Bio-Rad) using a transfer apparatus, PosiBlot (Stratagene). The plasmid pAG408 was labelled as the probe by random priming with the enhanced chemiluminescence kit (Amersham). The labelling, hybridisation and signal detection were conducted according to the manufacturer.

Catalase isozyme assay: *A. tumefaciens* strains A348, AG6, AG6 (pXQ23), AG6 (pXQ26), AG6 (pXQ27), AG6 (pXQ11), and AG6 (pXQ22) were grown overnight at 28° C. in MG/L liquid medium to 1.4 $OD_{600}$. The cells were harvested by centrifugation at 4000 rpm for 10 min at 4° C. The cell pellets were washed and resuspended in 5 ml extraction buffer containing 0.05 mM phosphate and 0.4 mM EDTA (pH 7.8). The cells were sonicated for 30 sec for 6 times on ice with a 2-min cooling on ice between sonications. The cell debris was removed by centrifugation at 1100 rpm for 10 min at 4° C. The cell-free supernatant was diluted 2× with the extraction buffer, and 20 µl of each diluted extract was electrophoresed on 7.5% native polyacrylamide gels. The resolving gel buffer was prepared at pH 8.1 instead of pH 8.9. Electrophoresis was performed at 150 V for 3 hours. Catalase isozymes were visualised by an activity staining procedure according to Clare et al. (1984).

Protein analysis: SDS/PAGE was conducted in 10% or 15% polyacrylamide gels to analyze the KatA or GFP expression, respectively. The proteins were transferred onto Immobilon-P membranes (Millipore). The KatA or GFP proteins were visualized with the enhanced chemiluminescence (ECL) western blot detection system according to the recommendations of the manufacturer (Amersham).

TABLE 1

Bacterial strains and plasmids used in this study

| Strain/plasmid | Relevant characteristics* | Source/Reference |
|---|---|---|
| Strains | | |
| *Agrobacterium tumefaciens* | | |
| A348 | Wild type, A136(pTiA6NC) (octopine-type) | Laboratory collection |
| AG6 | Derivative of A348 in which katA was disrupted by the GFP-tagged mini-Tn5 transposon at 995 bp downstream from the start condon of katA; $Km^R$, $Gm^R$ | This study |
| AG613 | AG6 containing pXQ13 integrated into the chromosome (containing a single copy of the wild type katA and katA-gfp fusion); KmR, $Gm^R$, $Cb^R$ | This study |
| CGI1 | Derivative of C58 in which aopB was disrupted by the GFP-tagged mini-Tn5 transposon; $Km^R$, $Gm^R$ | This study |

TABLE 1-continued

Bacterial strains and plasmids used in this study

| Strain/plasmid | Relevant characteristics* | Source/Reference |
|---|---|---|
| *Escherichia coli* | | |
| DH5a | supE Δlac(Δ80ZΔM15) hsdR recA endA gyrA thi relA | Bethesda Research Laboratories |
| MT607 | Pro-82 thi-1 hsdR 17 supE44 endA1 recA56 | Finan, et al., 1986 |
| Plasmids | | |
| pTZ19R | Cloning vector, ColE1 oriV bla, Amp$^R$ | US Biochemical |
| pSW172 | Broad-host-range IncP plasmid containing $P_{lac}$ and downstream polylinker sequence, Tc$^R$ | Chen and Winans, 1991 |
| pXQ6 | pBluescript II KS(-) containing a 6-kb ClaI DNA fragment containing the sequences downstream of the mini-Tn5 insertion at the katA gene. | This study |
| pXQ7 | pTZ19R containing a 5-kb NruI DNA fragment containing the sequences upstream of the mini-Tn5 insertion at the katA gene. | This study |
| pXQ9 | pSW172 carrying a 2.8 kb XbaI-NheI fragment containing the wild type katA, Tc$^R$ | This study |
| pXQ11 | pSW172 carrying a 2.3 kb XbaI-NheI fragment containing a KatA with a 86 amino acid deletion at the C-terminus, Tc$^R$ | This study |
| pXQ13 | pTZ19R carrying a 2.8 kb EcoRI fragment from pXQ9 containing the wild type katA, Amp$^R$ | This study |
| pXQ15 | pRSETA carrying a 2.17 kb XhoI-KpnI fragment containing the full length KatA ORF fused in-frame with (His)$_6$, Amp$^R$ | This study |
| pXQ22 | pSW172 carrying a 2.4 kb XbaI-NheI fragment containing a KatA with a 50 amino acid deletion at the C-terminus, Tc$^R$ | This study |
| pXQ23 | pSW172 ligated with pXQ13 at ClaI, containing the wild type katA, Amp$^R$ | This study |
| pXQ24 | pTZ19R carrying a 2.8 kb EcoRI fragment from pXQ9 containing a katA with His 98 replaced by Asp, Amp$^R$ | This study |
| pXQ25 | pTZ19R carrying a 2.8 kb EcoRI fragment from pXQ9 containing a katA with Arg 94 replaced by Gln and His 98 replaced by Asp, Amp$^R$ | This study |
| pXQ26 | pSW172 ligated with pXQ24 at ClaI, containing a katA with His 98 replaced by Asp, Amp$^R$, Tc$^R$ | This study |
| pXQ27 | pSW172 ligated with pXQ25 at ClaI, containing a katA with Arg 94 replaced by Gln and His 98 replaced by Asp, Amp$^R$, Tc$^R$ | This study |
| pXQ28 | pTZ19R carrying a 2.8 kb EcoRI fragment from pXQ9 containing the a katA with Ser5 replaced by a stop codon (TGA), Amp$^R$ | This study |
| pXQ29 | pTZ19R carrying a 2.8 kb EcoRI fragment from pXQ9 containing the a katA with a G base pair deletion in the second codon of katA ORF, Amp$^R$ | This study |
| pXQ30 | pSW172 ligated with pXQ29 at ClaI, containing a katA with a G base pair deletion in the second codon of katA ORF, Amp$^R$, Tc$^R$ | This study |
| pXQ31 | pSW172 ligated with pXQ28 at ClaI, containing a katA with Ser5 replaced by a stop codon (TGA), Amp$^R$, Tc$^R$ | This study |

Km, kanamycin; Tc, tetracycline; Amp, ampicillin; Gm, gentamycin.

Measurement of intracellular $H_2O_2$ concentrations: The intracellular concentrations of $H_2O_2$ were measured by the procedures previously described (González-Flecha and Demple, 1995; 1997) with modifications.

Briefly, *A. tumefaciens* strains A348, AG6 and AG6 (pXQ9) were grown at 28° C. for 24 hr on agar plates of AB or IB. The cells were harvested, washed and resuspended at $OD_{600}$=1.0 in 50 mM phosphate-buffer (pH 7.4). $H_2O_2$ generated within the cells passed through membranes and equilibrated with the buffer. Complete equilibration of the intracellular and extracellulare $H_2O_2$ levels occurred within 10 min in the assay (González-Flecha and Demple, 1997). After 20 min of equilibration, the cell suspensions were centrifuged for 1 min at 6,000 rpm at 4° C.

$H_2O_2$ concentrations in the supernatants were then measured by the Amplex Red Hydrogen Peroxide Assay Kit (Molecular Probes Inc., USA), which contains a highly sensitive and specific fluorogenic probe (N-acetyl-3,7-dihydroxyphenoxazine) for $H_2O_2$ and horse radish peroxidase (HRP) (Mohanty, et al, 1997). Briefly, 100 μl supernatant was mixed with 100 μl of the probe at 100 μM and 1 U/ml HRP. The fluorometric assay was conducted in a 96-well microplate and measured by Luminescence Spectrometer LS50B (Perkin Elmer). The excitation wavelength was 540 nm; the emission wavelength was 590 nm. The assays were run in four replicates; the concentrations were then calculated based on the $H_2O_2$ standard curves generated simutaneously.

Catalase activity assay: The catalase activity in whole bacterial cells was determined as previously described (Maciver and Hansen, 1996) except using the Amplex Red Catalase Assay Kit (Molecular Probes Inc., USA). Briefly, *A. tumefaciens* strains were grown at 28° C. for 24 hr on IB plates. The cells were harvested, washed and resuspended at $OD_{600}=1.0$ in 50 mM phosphate-buffer (pH 7.4). For the strains with the wild type katA [A348, AG6 (pXQ9), and AG6 (pXQ23)], 100 µl cell suspension of each sample was incubated with 50 µl 40 µM $H_2O_2$ at time intervals of 0, 30 sec, 1 min and 2 min.

For the strains with the katA mutants [AG6, AG6 (pXQ11), AG6 (pXQ22), AG6 (pXQ26) and AG6 (pXQ27)], 100 µl cell suspension of each sample was incubated with 50 µl 5 µM $H_2O_2$ at time intervals of 0, 1, 2, and up to 6 min. The amount of $H_2O_2$ left after degradation by the bacterial catalase was then determined by adding 50 µl Amplex Red reagent N-acetyl-3, 7-dihydroxyphenoxazine at 25 µM and 0.4 U/ml horse radish peroxidase provided by the kit. The fluorometric assay was conducted by the same procedure as described above for the measurement of intracellular $H_2O_2$. The cell suspensions without the added $H_2O_2$ were used as the blank. Solutions of crystalline bovine catalase (Sigma) were used to standardize this assay.

EXAMPLE 2

Cloning, Sequencing and Characterization of the katA Gene Encoding Catalase from *Agrobacterium*

The total DNA was extracted from AG6 which contains a mini-Tn5 insertion at the katA gene. Southern analysis revealed a 6-kb ClaI DNA fragment containing the sequences downstream of the mini-Tn5 insertion at the katA gene and a 5-kb NruI DNA fragment containing the sequences upstream of the insertion. Those DNA fragments were extracted from the agarose gels and were cleaned by using GENECLEAN II Kit (BIO 101). The ClaI DNA fragment was cloned into pBluescript II KS (–) at the ClaI site, and the NruI DNA fragment was cloned into pTZ19R at the SmaI site.

The resulting plasmids were designated as pXQ6 and pXQ7, respectively. Sequencing of pXQ6 and pXQ7 was carried out using a mini-Tn5 specific primer and the M13 reverse and –40 universal primers. The resulting sequence data were then used to generate primers for further sequencing. DNA sequencing was carried out using the ABI PRISM 377 DNA Sequencer.

In order to clone the full length katA gene, primers p83 (5'-GGTGCGCTAGCCAAATTCGTCACCAAGC-3') and n84 (5'-CAATCGCTAGCGTTCGGCCCTCTG-3') were designed that can respectively reanneal to the upstream and downstream sequences of the katA gene. Both primers had a NheI site to facilitate subsequent cloning. The total DNA from *A. tumefaciens* strain A348 was used as the template for PCR to amplify a 2.9 kb DNA fragment. The PCR product was digested with NheI and ligated into pSW172 (Chen and Winans, 1991) that had been digested with XbaI. The resulting plasmid pXQ9 was sequenced in both directions independently to obtain unambiguous sequence data. Plasmid pXQ9 was introduced into the mini-Tn5 mutant AG6 to create AG6 (pXQ9) by triparental mating (Ditta et al., 1980) based on selection on MG/L medium supplemented with 100 µg/ml of kanamycin and 5 µg/ml of tetracycline.

The following is a characterization of katA encoding catalase from Agrobacterium. *A. tumefaciens* A348 was mutagenized with a mini-Tn5 transposon containing a promoter-less gene encoding a green fluorescent protein (GFP) variant, which produces bright green fluorescence under UV light. The mini-Tn5 transposon was carried on a plasmid pAG408 (Suarez et al., 1997). One of the mutants AG6 contained the transposon insertion at a gene that was differentially induced by pH on a minimal medium.

The leaves of Kalanchoe plants were inoculated with this mutant strain AG6 and compared with the parent strain A348. AG6 was highly attenuated in the ability to cause tumors on plants as compared with A348. In order to isolate the mini-Tn5 containing DNA fragments, Southern analysis was conducted to estimate their sizes. A 6-kb ClaI DNA fragment containing the sequences downstream of the transposon insertion site and a 5-kb NruI DNA fragment containing the sequences upstream of the insertion site were cloned into the vectors, resulting in plasmids pXQ6 and pXQ7, respectively. Sequence analysis of pXQ6 and pXQ7 revealed that the transposon was inserted at a gene that is homologous to bacterial genes encoding catalases. This gene is designated as katA.

Figure 1:
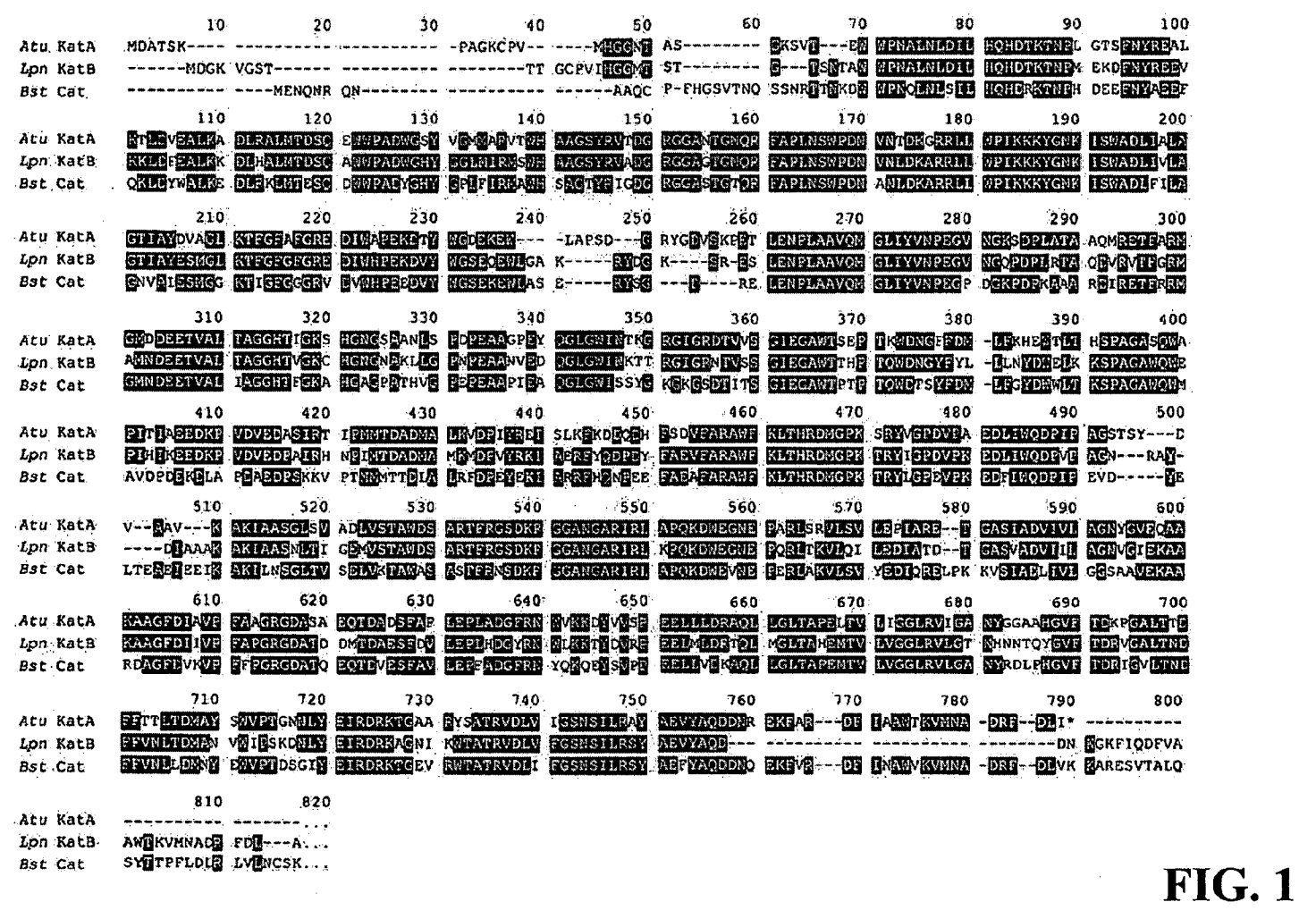

In order to determine the complete sequence of the gene, the DNA fragment was amplified from A348 by polymerase chain reaction (PCR). A fragment of 2.9 kb was obtained that contained both the upstream and downstream sequences of katA. The resulting fragment was cloned into pSW172 (Chen and Winans, 1991) to generate plasmid pXQ9. When pXQ9 was introduced into AG6, it could fully restore the ability of the mutant to cause tumors, suggesting that pXQ9 carried a full length katA gene. Sequence analysis indicated that the katA locus carried a single open reading frame (ORF) which encodes a putative protein of 723 amino acids with a molecular weight of 78.7 kDa. This putative protein was highly homologous to other bacterial catalases (FIG. 1).

To determine whether the katA gene encodes a functional catalase, the catalase isozyme patterns were analyzed for the mutant, parent strain and complemented strain by using a catalase activity staining procedure. As shown in FIG. 2A, both the parent strain A348 and the complemented strain AG6 (pXQ9) had three distinct catalase activity bands (I, II and III), whereas the mutant AG6 had only one band (I). This demonstrated that the transposon insertion at the katA gene in AG6 knocked out two catalase activity bands.

To investigate whether these two catalase activity bands originated from the same katA gene, different amounts of the bacterial cell extracts were loaded on the polyacrylamide gels for the catalase activity staining. It was found that the catalase activity band III disappeared even in A348 when less amount of the cell extract was loaded (FIG. 2B). This suggests that the catalase activity bands II and III originated from the same katA gene product. The catalase activity band III appeared only when a sufficient amount of cell extract was loaded, suggesting that the band III was an aggregated form of catalase activity band II.

It was important to determine whether this katA gene encoded a protein that possessed both catalase and peroxidase activities like some of the catalase genes (Loewen, 1997). When the peroxidase activities with the same cell extracts were stained (Gregory and Fridovich, 1974), no peroxidase activity was found to be associated with the catalase activity bands. Taken together, these suggest that the katA gene encodes a catalase isozyme in the *A. tumefaciens* cells.

EXAMPLE 3

Determination of katA-gfp Expression Based on GFP

To study the katA gene expression in different growth conditions, *A. tumefaciens* strains A348 and AG6 were grown at 28° C. for 24 hr on agar plates of MG/L, AB, IB (Cangelosi et al., 1991), and fresh Kalanchoe leaf tissue and stem tissue sections which were sterile and placed on MS medium (Murashige and Skoog, 1962). The cells were harvested, washed and diluted to a concentration of approximately $OD_{600}$=0.5. The fluorescence of each cell suspension was measured by Luminescence Spectrometer LS50B (Perkin Elmer) using A348 as the blank. The excitation wavelength was 423 nm; the emission wavelength was 509 nm. The fluorescence levels were expressed as the fluorescence values divided by the corresponding $OD_{600}$.

To study the katA gene expression in different genetic backgrounds, *A. tumefaciens* strains A348, AG6, AG6 (pSW172), AG6 (pXQ9), A613, CGI1 and CGI1 (pXQ9) were grown at 28° C. for 24 hours on IB (pH 5.5) agar plates. The fluorescence of each strain was determined as described above.

To determine if $H_2O_2$ can induce the katA expression, AG6 was grown in MG/L liquid medium overnight at 28° C. The cells were harvested and resuspended in fresh MG/L liquid medium to a final concentration of $OD_{600}$=0.5. Aliquots (2 ml) of the cultures were transferred into sterile tubes, and $H_2O_2$ was added to the tubes to final concentrations of 30 µM, 60 µM and 120 µM. The cell suspensions were incubated at 28° C. for 2 hours. Then 1 ml of each cell suspension was centrifuged, washed and resuspended in the Laemmli (1970) sample buffer, and subjected to Western blot as described later.

EXAMPLE 4

Mutagenesis

The C-terminus of KatA was deleted by PCR to generate pXQ11 and pXQ22. Site-directed mutagenesis of katA was performed by overlap extension PCR (Ho et al, 1989). Four oligonucleotides were designed to mutate a single one amino acid of the KatA protein. Two residues Arg 94 and His 98 in the putative catalase motif are highly conserved. His 98 was changed to Asp; alternatively, Arg 94 was changed to Gln and His 98 was changed to Asp. A 450 bp NsiI -AatII PCR fragment containing a single mutation at His 98 or double mutations at both His 98 and Arg 94 was used to replace the corresponding NsiI -AatII fragment of pXQ13 containing the wild-type katA, in order to generate pXQ24 or pXQ25, respectively. The presence of the expected point mutations in NsiI-AatII fragment was confirmed by DNA sequencing using the ABI PRISM 377 DNA Sequencer. Similarly, A 670 bp MfeI-AatII PCR fragment containing an introduced stop codon at Ser 5 or a frameshift deletion at the second codon of the katA ORF was used to replace the corresponding MfeI-AatII fragment of pXQ13 containing the wild-type katA, to generate pXQ28 and pXQ29, respectively.

EXAMPLE 5

Purification of His-KatA Fusion Protein and Generation of Antibody to KatA

To generate a $(His)_6$-KatA fusion construct, an oligomer (containing XhoI site) complementary to the start of the KatA ORF and an oligomer (containing KphI site) was used to amplify the KatA ORF fragment. The 2.17 kb XhoI-KpnI fragment was inserted in-frame downstream of $(His)_6$ harbored on pRSETA. The resulting pXQ15 was introduced into BL21 by tranformation. BL21 (pXQ15) was grown overnight in LB medium in the presence of 100 µg/ml of carbenicillin at 37° C. The cell culture was harvested. Purification of $(His)_6$-KatA was conducted with TALON metal affinity resin according to the manufacturer (Clontech). The purified protein was injected into rabbits to generate the primary antibody. Protein analysis of KatA or GFP was carried out as described above.

EXAMPLE 6

Complementation

Plasmids pXQ13, pXQ24, pXQ25, pXQ28 and pXQ29 were digested by ClaI and ligated with ClaI digested pSW172 to generate pXQ23, pXQ26, pXQ27 pXQ30 and pXQ31. Plasmids pSW172, pXQ11, pXQ22, pXQ23, pXQ26, pXQ27, pXQ30 and pXQ31 were introduced into the mini-Tn5 mutant AG6 by triparental mating (Ditta et al., 1980) or electroporation (Cangelosi et al., 1991). Plasmid pXQ13 was introduced into AG6 by electroporation, followed by selection in the presence of carbenicillin. The resulting strain AG613 was obtained that underwent a single crossover homologous recombination at the katA locus; it was confirmed by Southern analysis. These transformant strains were analyzed for the GFP and KatA expression levels.

The intracellular concentrations of $H_2O_2$ were measured according to the technique described above in Example 1 ("Measurement of intracellular $H_2O_2$ concentrations").

The catalase activity in whole bacterial cells was determined as described above in Example 1 ("Catalase activity assay").

EXAMPLE 7

Intercellular Repression of katA-gfp Expression

To determine whether catalase activity of one bacterial cell could affect the katA-gfp gene expression of another cell, AG6 was co-cultured with other bacteria which contained catalase activity. The bacterial cells grown overnight were suspended in IB liquid and adjusted to $OD_{600}$=1.0. The AG6 cell suspension was mixed with another bacterial suspension at 1:1 ratio. An aliquot of 12 µl bacterial suspension of a single strain or a mixture of two strains was spotted onto IB plates. The plates were incubated overnight at 28° C.

The bacterial fluorescence under UV light was photographed and the intensity for GFP expression was measured by the procedure described earlier. To check the growth viability of each strain in the co-culture mixture, a portion of each co-culture mixture was harvested to test the viable cell count on MG/L (for total viable cell count) and MG/L supplemented with 100 µg/ml kanamycin (for AG6 viable cell count)

EXAMPLE 8 katA is Inducible by Acidic pH

*A. tumefaciens* mutant AG6 contained a mini-Tn5 transposon containing a promoter-less green fluorescent protein (GFP) variant; the mini-Tn5 transposon was inserted at 995 bp downstream from the start codon of katA. Since the gfp gene was under the control of the katA promoter (designated as katA-gfp), the katA expression would lead to the accumulation of GFP, which could be visualized as bright green fluorescence under UV light. Therefore, the differential expression of katA in *A. tumefaciens* could be determined by measuring the GFP expression of the mutant AG6 in different conditions.

Figure 3:
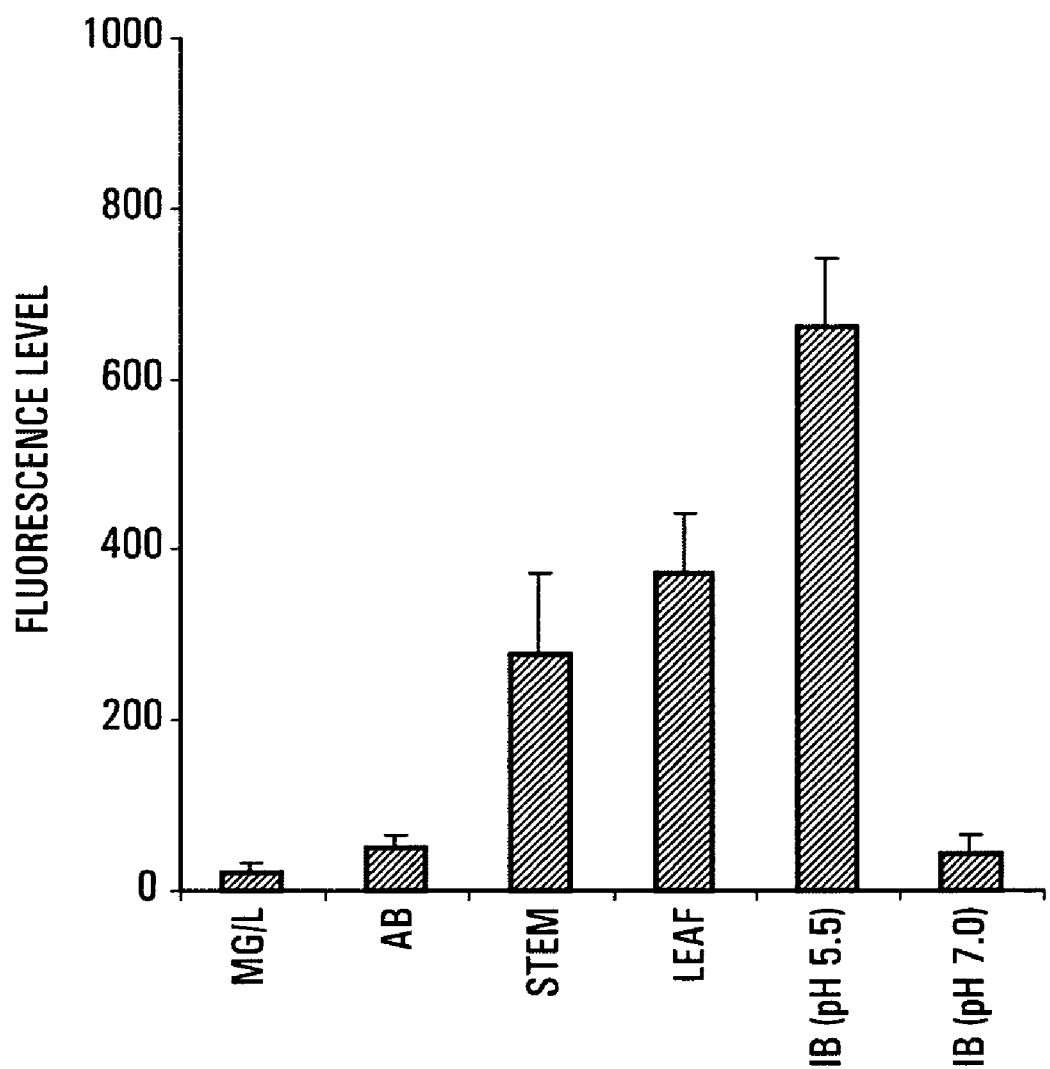
FIG. 3. The katA-gfp expression in different growth media. *Agrobacterium tumefaciens* strains A348 and AG6 were grown at 28° C. for 24 hr on agar plates of MG/L, AB, IB (pH 5.5), and IB (pH 7.0) and fresh Kalanchoe leaf tissue and stem tissue sections. The cells were harvested and then resuspended in $dH_2O$. The fluorescence of each cell suspension was measured by Luminescence Spectrometer LS50B (Perkin Elmer) as described in the Materials and Methods using A348 as the blank.

The katA-gfp expression was examined by growing AG6 on different growth media, MG/L (a rich medium; pH 7.0), AB (a minimal medium; pH 7.0), and IB (a minimal medium; pH 5.5), as well as on fresh Kalanchoe leaf tissue and stem tissue sections. As shown in FIG. 3, the fluorescence level of the bacteria grown on IB was about 10-20 fold higher than that on neutral pH media including AB and MG/L. The fluorescence levels on Kalanchoe leaf tissue and stem tissue sections were about 5-10 fold higher than those in the neutral pH media. This indicates that katA might be induced by acidic pH, as the plant tissues also have acidic pH and minimal nutrition (Li et al., 1999).

Previous experiments have demonstrated that IB medium is representative of the growth conditions the bacteria encounter inside plant tissues during the infection process (Li et al., 1999). To confirm that acidic pH can induce the katA expression, the fluorescence level on IB (pH 5.5) was compared with that on the medium having the same IB ingredients but with the pH adjusted to pH 7.0 (IB pH 7.0). As shown in FIG. 3, the fluorescence level on IB (pH 7.0) was reduced to a level that was similar to other neutral media, including AB and MG/L. This demonstrates that acidic pH can induce the katA expression.

EXAMPLE 9

Repression of katA-gfp Expression by katA

Figure 4:
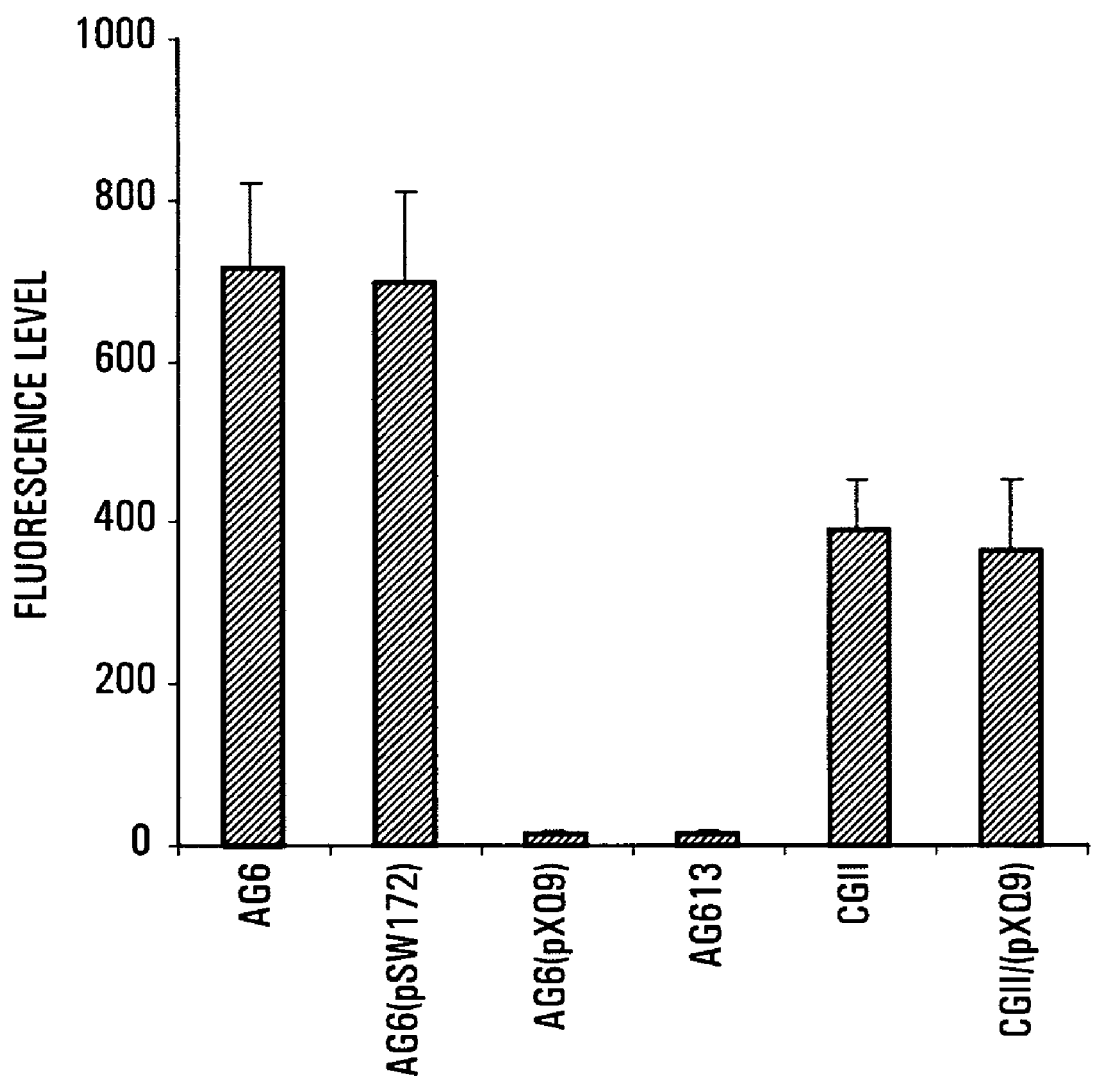
FIG. 4. Comparison of katA-gfp expression in different genetic backgrounds. *Agrobacterium tumefaciens* strains A348, AG6, AG6 (pSW172), AG6 (pXQ9), AG613, CGI1 and CGI1 (pXQ9) were grown at 28° C. for 24 hr on agar plates of IB (pH 5.5). The cells were harvested and then resuspended in dH$_2$O. The fluorescence of each cell suspension was measured by Luminescence Spectrometer LS50B (Perkin Elmer) as described in the Materials and Methods using A348 as the blank.

As shown earlier, the plasmid pXQ9 which carried a full-length katA gene could fully complement the katA mutation. When the fluorescence level in the complemented strain AG6 (pXQ9) was analyzed, it was surprisingly found that this strain had a highly reduced fluorescence (60-70 fold reduction, as shown in FIG. 4). It appeared that the wild type katA could repress the katA-gfp expression.

To determine if katA could specifically repress katA-gfp, pXQ9 was introduced into a different mini-Tn5 transposon mutant strain CGI1, which contained the transposon insertion at a chromosomal gene aopB and could produce bright green fluorescence under UV light. As shown in FIG. 4, the katA gene did not repress the aopB-gfp expression. This suggests that katA can specifically repress katA-gfp expression.

It was of interest to determine whether the copy number and the location of katA could affect the ability to repress. katA was integrated into the chromosome of AG6 through single-crossover homologous recombination. The resulting strain AG613 contained a single copy of the wild-type katA and a single copy of the katA-gfp fusion as verified by Southern analysis. AG613 had a very low level of katA-gfp expression, just like AG6 (pXQ9) harboring the katA gene on a plasmid (FIG. 4). This suggests that only one copy of katA was sufficient to repress the katA-gfp expression, no matter whether katA is located on plasmid or chromosome.

EXAMPLE 10

Requirements of the katA-gfp Repression

Figure 5:
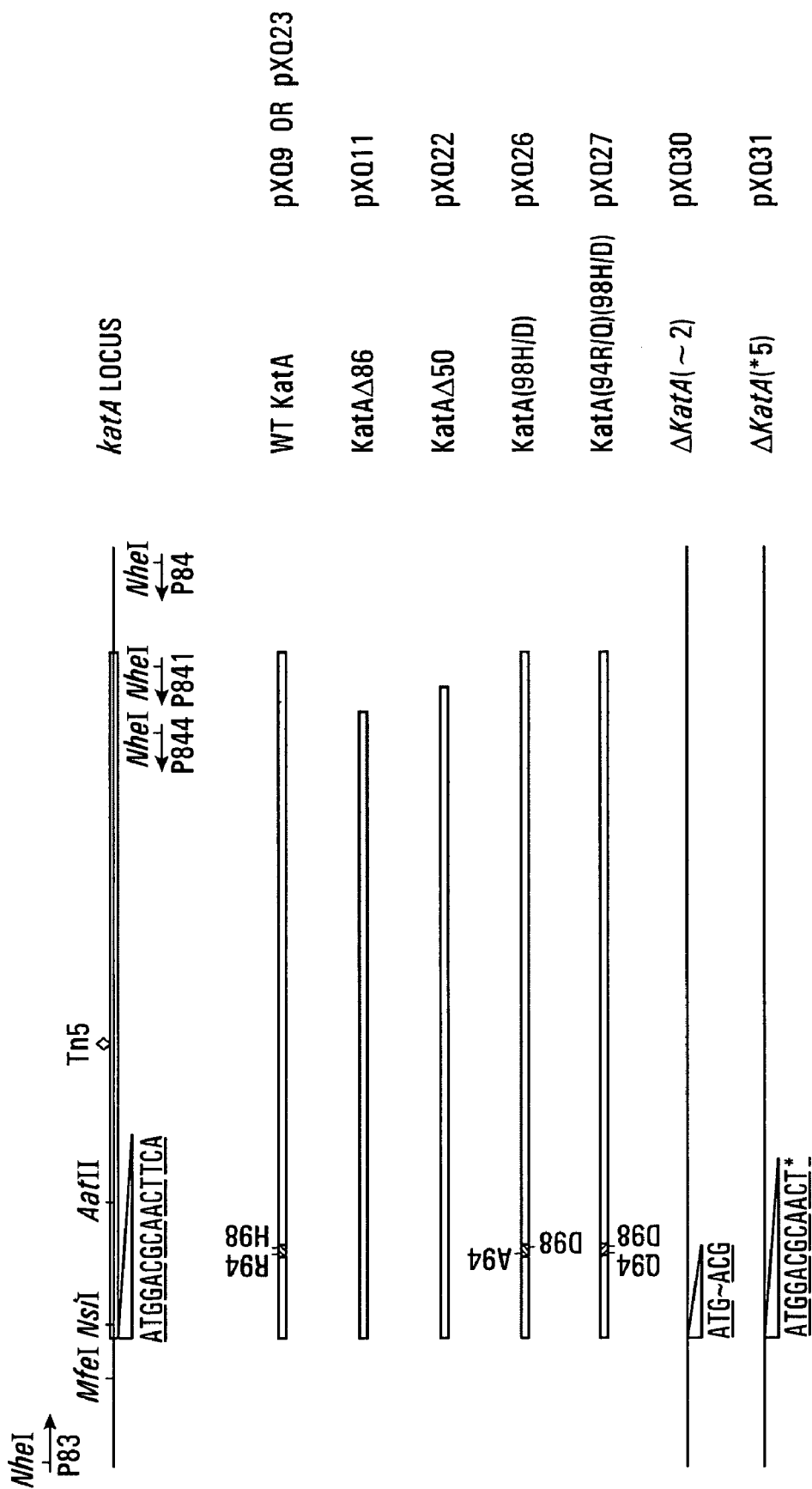
FIG. 5. Schematic presentation of the wild-type and mutated katA genes. The lines represent the DNA sequences; the boxes represent the KatA open reading frames (ORFs). The vertical lines indicate the restriction sites or amino acid positions. The diamond indicates the mini-Tn5 transposon insertion position. The key restriction endonuclease sites and primers used are indicated. The DNA sequences under the triangles are the ORF sequences concerned for the site-directed mutagenesis. ~ represents a deletion of the G of the second codon; * represents the stop codon introduced at the fifth codon. The wild type katA in pXQ9 and the mutant katA genes encoding KatAΔ50 and KatAΔ86 were driven by the katA promoter. The wild type katA in pXQ23 and the mutant genes encoding KatA (98H/D), KatA (94R/Q) (98H/D), ΔkatA (~2) and ΔkatA (*5) were driven by both the katA and lac promoter.

It was of interest to determine if the repression by katA occurred at the mRNA level or protein level. Site-directed mutagenesis was conducted to generate mutants that produced no or truncated KatA protein. The C at the nucleotide position 14 within the katA open reading frame (ORF) was changed to G. This created a stop codon at Ser 5 [designated as ΔkatA (*5)]; the resulting plasmid was named (pXQ31) (FIG. 5; Table 1). A frameshift deletion at katA was then created by deleting the G of the second codon in the katA ORF [designated as ΔkatA (~2)]; the resulting plasmid was named pXQ30 (FIG. 5).

Figure 6A:
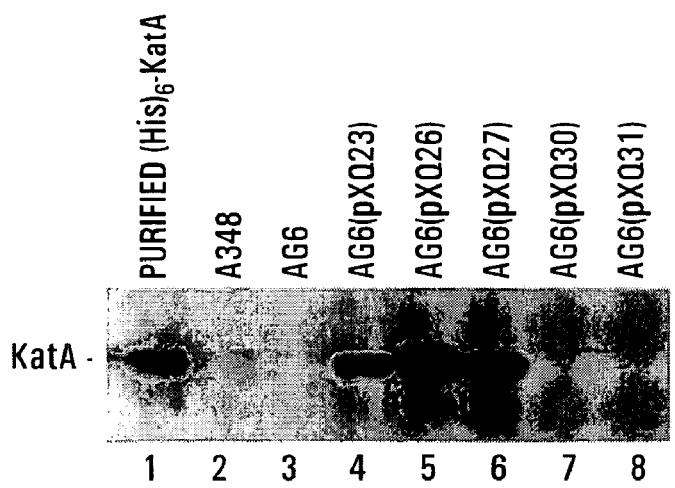
FIG. 6. The effects of katA mutations on the KatA protein stability. *Agrobacterium tumefaciens* strains A348 (panel A, lane 2; panel B, lane 1), AG6 (panel A, lane 3), AG6 (pXQ23) (panel A, lane 4), AG6 (pXQ26) (panel A, lane 5), AG6 (pXQ27) (panel A, lane 6), AG6 (pXQ30) (panel A, lane 7), AG6 (pXQ31) (panel A, lane 8), AG6 (pXQ9) (panel B, lane 2), AG6 (pXQ11) (panel B, lane 3), and AG6 (pXQ22) (panel B, lane 4) were grown overnight at 28° C. on IB plates. The cells were harvested, washed and diluted to a concentration of OD$_{600}$=0.3. The cells from 500 µl of cell suspensions were harvested by centrifugation and resuspended in the Laemmli (1970) sample buffer. An aliquot of 2 µl of each sample was electrophoresed on SDS/10% PAGE gels. The proteins were transferred onto Immobilon-P membrane and visualized by (His)$_6$-KatA antibody. The purified (His)$_6$-KatA was used as the control.
Figure 6B:
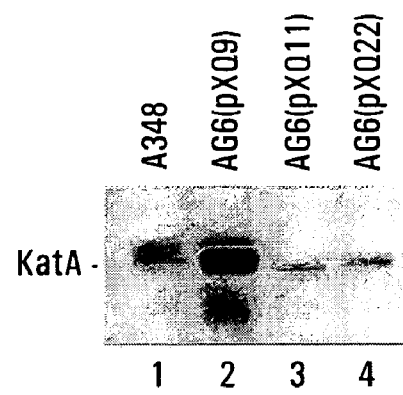
Figure 7:
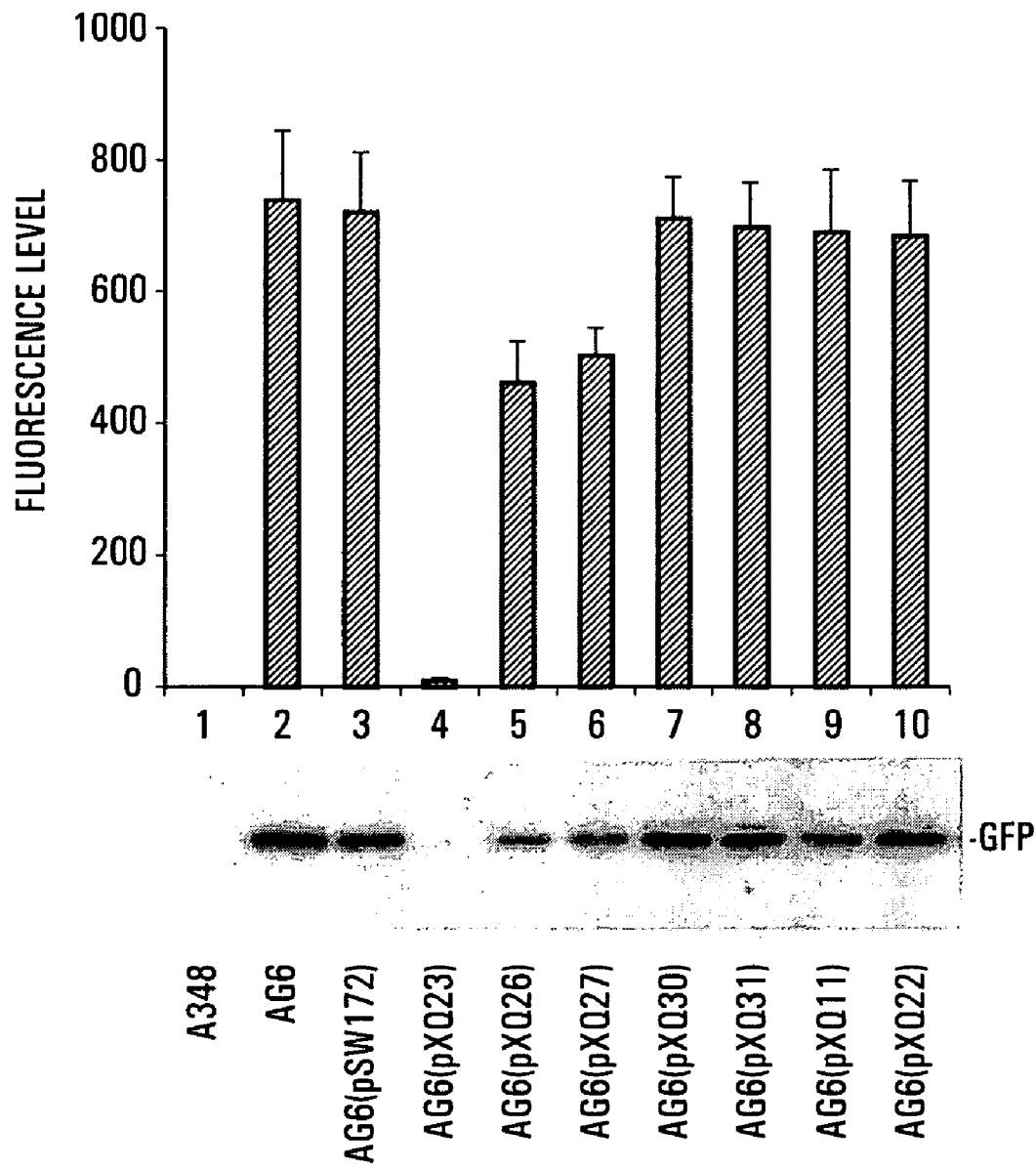
FIG. 7. Detection of the GFP protein expression of the katA-gfp fusion. *Agrobacterium tumefaciens* strains A348 (lane 1), AG6 (lane 2), AG6 (pSW172) (lane 3), AG6 (pXQ23) (lane 4), AG6 (pXQ26) (lane 5), AG6 (pXQ27) (lane 6), AG6 (pXQ30) (lane 7), AG6 (pXQ31) (lane 8), AG6 (pXQ11) (lane 9), and AG6 (pXQ22) (lane 10) were grown overnight at 28° C. on IB plates. The cells were harvested and then resuspended in dH$_2$O. One portion of each cell suspension was used to measure the fluorescence by Luminescence Spectrometer LS50B (Perkin Elmer) as described in the Materials and Methods using A348 as the blank (upper panel). Another portion of each cell suspension was diluted to a concentration of OD$_{600}$=0.3. The cells from 500 µl of cell suspensions were harvested by centrifugation and resuspended in the Laemmli (1970) sample buffer. An aliquot of 2 µl of each sample was electrophoresed on SDS/15% PAGE gels. The proteins were transferred onto Immobilon-P membrane; the GFP was visualized by the GFP antibody (lower panel).

As shown in FIG. 6, the pXQ31 construct did not generate any KatA protein. pXQ30 generated a trace amount of KatA-like protein, presumably produced from an alternative translation site downstream from the start codon or due to infrequent frame shifting of the ribosome, which could restore the translation of the protein. These two constructs did not repress the katA-gfp expression as determined by both the GFP fluorescence and western analysis using the antibody to GFP (FIG. 7). This suggests that production of the KatA protein is required for the repression.

It was then important to determine whether a full-length KatA polypeptide was required for the repression. The 86 amino acids (designated as KatAΔ86) and 50 amino acids (KatAΔ50) at the C-terminus of KatA were deleted to generate pXQ11 and pXQ22, respectively (FIG. 5). These constructs produced smaller sizes of KatA proteins as expected (FIG. 6B, lanes 3 and 4). However, the amounts of these truncated KatA proteins were much less than the wild type KatA (harbored on pXQ9) (lane 2), indicating that these truncated KatA proteins were unstable. These truncated proteins did not repress the katA-gfp expression at a significant level (FIG. 7, lanes 9 and 10), presumably because they did not exhibit any significant catalase activity (FIG. 8; Table 2).

TABLE 2

Catalase activity in whole bacterial cells containing the wild type or mutant katA genes[a]

| Strain | Protein expressed | Catalase activity (unit/10⁸ cells) |
| --- | --- | --- |
| AG6(pXQ23) | KatA | 77145.5 ± 440.3 |
| AG6(pXQ9) | KatA | 3997.3 ± 459.1 |
| A348 | KatA | 1486.2 ± 149.5 |
| AG6(pXQ26) | KatA(98H/D) | 219.3 ± 19.5[b] |
| AG6(pXQ11) | KatAΔ86 | 193.6 ± 25.2[c] |
| AG6(pXQ27) | KatA(94R/Q)(98H/D) | 184.0 ± 25.1[c] |
| AG6(pXQ22) | KatAΔ50 | 182.7 ± 21.5[c] |
| AG6 | KatA | 175.2 ± 20.2[c] |

[a]*Agrobacterium tumefaciens* cells were grown on IB plates and then harvested. The catalase activities in whole bacterial cells were measured as described in the Materials and Methods.
[b]The catalase activity of AG6(pXQ26) was significantly different from that of AG6(P < 0.05) based on Student's t-test.
[c]The catalase activity of AG6(pXQ11), AG6/(pXQ27) or AG6/(pXQ22) was not significantly different from that of AG6 based on Student's t-test.

Since the truncated KatA proteins did not possess any catalase activity detected by an isozyme staining procedure (FIG. 8), it was important to know whether a functional catalase activity was required for this feedback repression. The amino acid sequence of *A. tumefaciens* catalase KatA was analyzed by a motif search program (http://www.motif-.genome.ad.jp). It revealed that a motif of 12 amino acids (VGMMARVTWHAA) located from amino acid 89 to 100 from the start codon was qualified for a peroxidases active site signature. This motif might be involved in the catalase activity.

Site-directed mutagenesis was conducted to inactivate the catalase activity. Computer analysis revealed that Arg 94 and His 98 in the conservative motif of KatA might be crucial for the catalase activity. Previous studies have indicated that the corresponding residues Arg 102 and His 106 of the *E. coli* homolog HPI are important for the catalase activity (Hillar et al., 2000). His 98 was changed to Asp [designated as KatA (98H/D)]; Arg 94 was changed to Gln and His 98 was changed to Asp [designated as KatA (94R/Q) (98H/D)]. The resulting plasmids were named pXQ26 and pXQ27, respectively.

Figure 8:
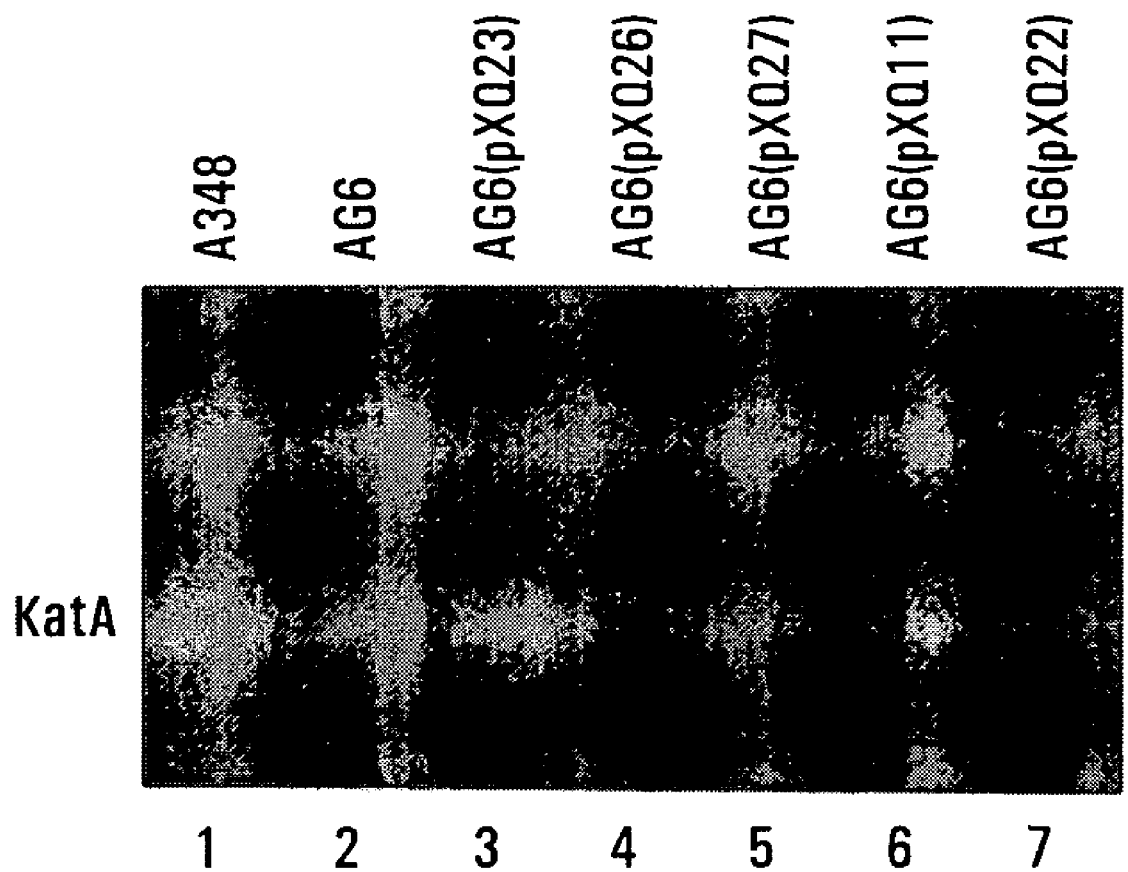
FIG. 8. Assays for catalase activity bands. *Agrobacterium tumefaciens* strains A348 (lane 1), AG6 (lane 2), AG6 (pXQ23) (lane 3), AG6 (pXQ26) (lane 4), AG6 (pXQ27) (lane 5), AG6 (pXQ11) (lane 6), and AG6 (pXQ22) (lane 7) were grown overnight at 28° C. in MG/L liquid medium. Samples of crude cell extracts were prepared and electrophoresed on 7.5% nondenaturing gel as described previously (Xu and Pan, 2000). Catalase isozymes were visualized by activity staining according to Clare et al (1984). Since AG6 (pXQ23) was over-expressing KatA, this sample was diluted 8 fold before loading.

As shown in FIG. 8, both the wild-type strain A348 and the complemented strain AG6 (pXQ23) had the KatA catalase activity bands, whereas they were missing in the mutant AG6, AG6 (pXQ26) and AG6 (pXQ27). This suggests that alteration of His 98 or both Arg 94 and His 98 in the conservative motif of KatA abolished the KatA catalase activity detected by the staining procedure. Western blot analysis was performed to check the stability of the mutant proteins. As shown in FIG. 6A, AG6 (pXQ26) and AG6 (pXQ27) produced the same size of KatA proteins as the wild type, and a high level of the point mutant proteins accumulated in the cells. As shown in FIG. 7, these two point mutant proteins could slightly repress the katA-gfp expression. The GFP expression was virtually undetectable in AG6 (pXQ23) (lane 4), but it was reduced in AG6 (pXQ26) and AG6 (pXQ27) (lanes 5 and 6), as compared with the strains expressing no or truncated protein KatA (lanes 7, 8, 9 and 10).

It was important to determine if the mutant KatA proteins possessed any trace amount of catalase activity. The genes encoding those mutant proteins were introduced into AG6 that lacks katA. Then the catalase activity in whole bacterial cells was measured, because this could presumably avoid any inactivation of catalase activity due to the cell break-up process.

As shown in Table 2, the catalase activity in the bacteria containing the mutant protein, KatAΔ86, KatA (94R/Q) (98H/D) or KatAΔ50 was slightly higher than that in AG6, but not at a statistically significant level. This suggests that these mutant KatA proteins did not possess any significant catalase activity. The activities in whole cells for those bacteria were apparently due to the catalase other than KatA, since AG6 (which lacks katA) possessed catalase activity (FIG. 8 and Table 2). The catalase activity in AG6 (pXQ26) was statistically higher than that of AG6, suggesting that KatA (98H/D) possessed a low level of catalase activity. This low activity presumably has contributed to the low repression of katA-gfp (FIG. 7).

It is interesting to note that KatA (94R/Q) (98H/D) [in the strain AG6 (pXQ27)] repressed the expression of katA-gfp at a low level (FIG. 7), since the activity for this protein was not statistically significant and was lower (if any) than that of KatAΔ86 (Table 2), which did not repress the katA-gfp expression at a significant level (FIG. 7). This suggests that both the KatA catalase activity and the protein itself were involved in the repression of katA-gfp.

In summary, the repression of katA-gfp expression required the production of a functional KatA protein that possessed the catalase activity. In addition, among the mutant KatA proteins only KatA (98H/D) and KatA (94R/Q) (98H/D) could significantly repress the katA-gfp expression at a level much lower than the wild-type KatA (FIG. 7). Incidentally, only these two mutant KatA proteins accumulated at a very high level in the bacteria (FIG. 6). This suggests that the sheer amount of the KatA proteins present in the cells might contribute to the repression, presumably because the mutant KatA proteins could still bind to $H_2O_2$ to reduce the availability of intracellular $H_2O_2$ to induce katA-gfp expression. KatA (98H/D) repressed the katA-gfp expression at a level slightly higher than KatA (94R/Q) (98H/D) (FIG. 7), presumably due to its low catalase activity while KatA (94R/Q) (98H/D) did not possess any significant catalase activity (Table 2) because both two important residues at the putative active site have been altered (FIG. 5).

EXAMPLE 11 katA Can Be Induced by Hydrogen Peroxide

It was then important to determine how the catalase activity repressed the katA-gfp expression. One possibility is that catalase may reduce the intracellular $H_2O_2$ levels to repress the katA-gfp expression. To determine whether the expression of katA can be induced by $H_2O_2$, like some of other bacterial catalases (Loewen, 1997), AG6 was treated with low concentrations of $H_2O_2$ (30-120 μM) in liquid MG/L medium and the katA-gfp expression levels were then determined.

Figure 9:
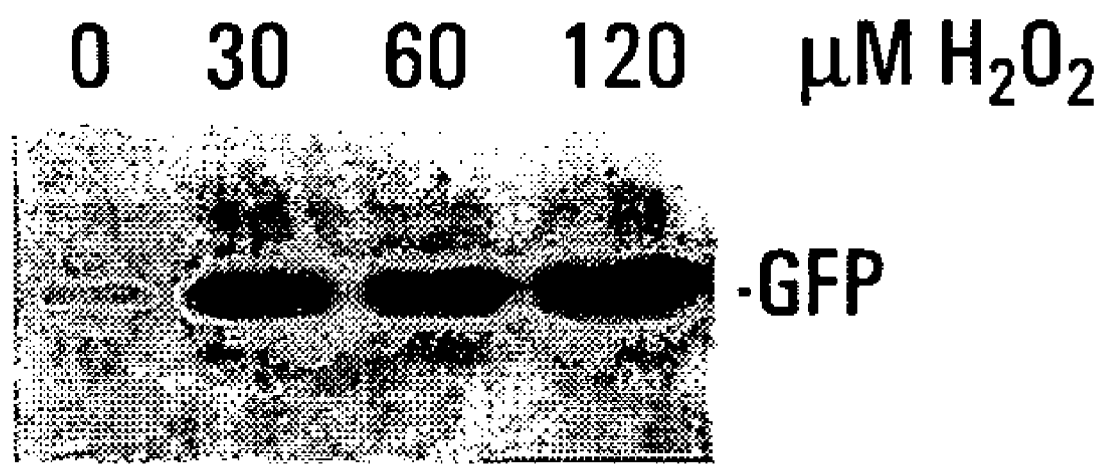
FIG. 9. Induction of the katA-gfp fusion by H$_2$O$_2$. The cells of *Agrobacterium tumefaciens* AG6 grown in MG/L (OD$_{600}$=0.5) were exposed to 0, 30 µM, 60 µM, and 120 µM H$_2$O$_2$. The cell suspensions were incubated at 28° C. for 2 hours. Aliquots of 1 ml cell cultures were harvested by centrifugation and resuspended in the Laemmli (1970) sample buffer. An aliquot of 10 µl of each sample was electrophoresed on SDS/15% PAGE gels. The proteins were transferred onto Immobilon-P membrane; the GFP was visualized by the GFP antibody.

As shown in FIG. 9, the katA-gfp expression levels increased significantly in the presence of $H_2O_2$, suggesting that the katA expression could be induced by $H_2O_2$. This indicates that the reason that the catalase activity could repress the katA-gfp expression is that catalase could deplete the katA inducer level. This implies that the endogenous $H_2O_2$ acts as the intracellular inducer for the katA expression inside *A. tumefaciens* cells and that induction of katA by acidic pH involves the increase of intracellular $H_2O_2$ levels.

EXAMPLE 12

Acidic pH Could Enhance the Accumulation of Intracellular $H_2O_2$ in katA Cells Since katA could be induced by $H_2O_2$, it was important to determine whether the induction of katA by acidic pH was indeed due to the enhanced levels of endogenous $H_2O_2$ in the bacterial cells. The intracellular $H_2O_2$ concentrations were measured for the bacteria grown on the acidic IB plates (pH 5.5) or AB plates of neutral pH (pH 7.0), according to the previously described procedures (González-Flecha and Demple, 1995; 1997) that were based on a complete equilibration of the intracellular and extracellular $H_2O_2$ levels of the bacterial cells that were grown on IB or AB and then resuspended in a phosphate buffer (pH 7.4) (see the Materials and Methods).

As shown in Table 3, the intracellular $H_2O_2$ concentration for the AG6 cells grown on IB was about 10 times higher than those for the bacterial cells containing the wild-type katA [A348 and AG6 (pXQ9)]. The level for the AG6 cells grown on AB was about 4 times higher than those for the bacteria having the wild type katA. The level of intracellular $H_2O_2$ increased about 3 times when the AG6 cells were switched from pH 7.0 to pH 5.5. The intracellular $H_2O_2$ concentrations were virtually constant for the bacteria having the wild type katA, no mater whether they were grown on AB or IB plates. These indicate that mutation at katA enhanced the accumulation of intracellular $H_2O_2$ for the bacteria grown at acidic pH. The elevated level of intracellular $H_2O_2$ caused by acidic pH in the absence of functional katA induced the expression of katA-gfp.

TABLE 3

Intracellular $H_2O_2$ concentrations of bacteria grown on IB and AB plates[a]

| Strain | $H_2O_2$(μM) | |
|---|---|---|
| | AB (pH 7.0) | IB (pH 5.5) |
| A348 | 0.12 ± 0.03 | 0.13 ± 0.02 |
| AG6 | 0.41 ± 0.08 | 1.16 ± 0.14 |
| AG6(pXQ9) | 0.10 ± 0.02 | 0.09 ± 0.01 |

[a]*Agrobacterium tumefaciens* cells were grown on AB or IB plates. The intracellular $H_2O_2$ concentrations were measured as described in the Materials and Methods, based on a complete equilibration of the intracellular and extracellular $H_2O_2$ levels of the bacterial cells that were grown on IB or AB and then resuspended in a phosphate buffer (pH 7.4).

EXAMPLE 13

Intracellular $H_2O_2$ Scavenging Assay Technology

The studies indicate that mutation at katA can enhance the accumulation of intracellular $H_2O_2$ in the bacterial cells grown at acidic pH. The elevated level of intracellular $H_2O_2$ caused by acidic pH in the absence of functional katA can induce the expression of katA-gfp. When a katA gene encoding a functional catalase is introduced into the cells lacking the katA gene, katA-gfp expression is dramatically repressed (FIGS. 4, 7, 8 and 10).

Two mutant KatA proteins truncated at the C-terminus exhibited a very low level of accumulation in the cells and no significant catalase activity; neither mutant repressed katA-gfp expression at any significant level (FIGS. 7 and 8; Table 2). These indicate that the katA-gfp expression levels can reflect the intracellular $H_2O_2$ scavenging capacity of the cells. If the cells are introduced with molecules, large or small, that can scavenge the intracellular $H_2O_2$ levels, the katA-gfp expression will be repressed. Therefore, measuring the katA-gfp expression can monitor the intracellular $H_2O_2$ scavenging capacity of a molecule that is introduced into the cells.

Figure 10:
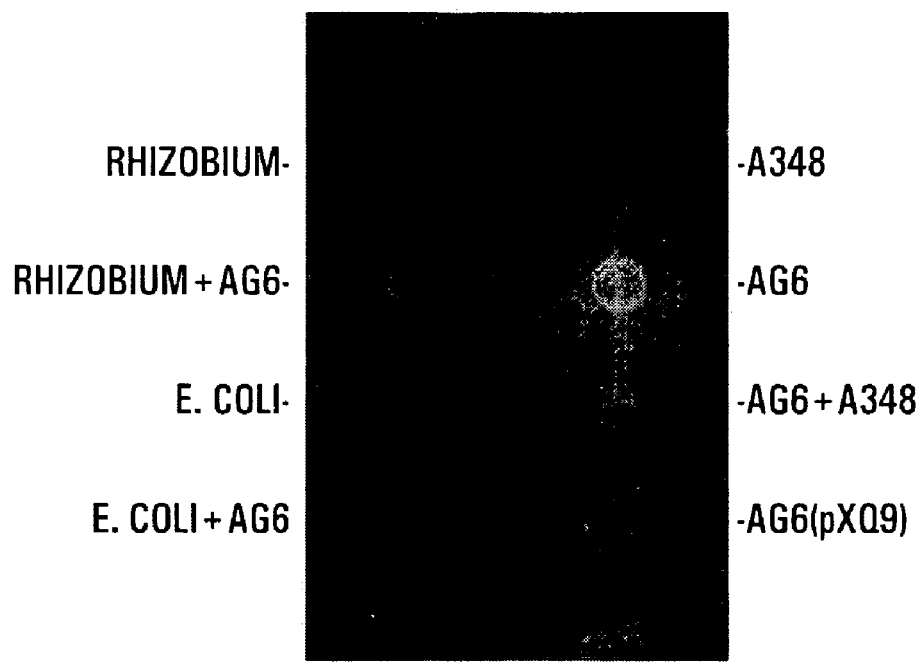
FIG. 10. Repression of katA-gfp expression by surrounding bacterial cells. The AG6 cells were mixed with at 1:1 ratio with the cells from the bacterial strains A348, *Rhizobium meliloti* RCR2011, or *E. coli* DH5α; the mixtures were spotted on IB plates. The same amount of bacterial cells from a single strain A348, AG6 (pXQ9), *Rhizobium meliloti* RCR2011, or *E. coli* DH5α was also spotted on IB plates. The plates were incubated overnight at 28° C. The bacterial fluorescence under UV light was photographed (upper panel). The fluorescence intensity was measured (lower panel) as described in the Materials and Methods.
Figure 10:
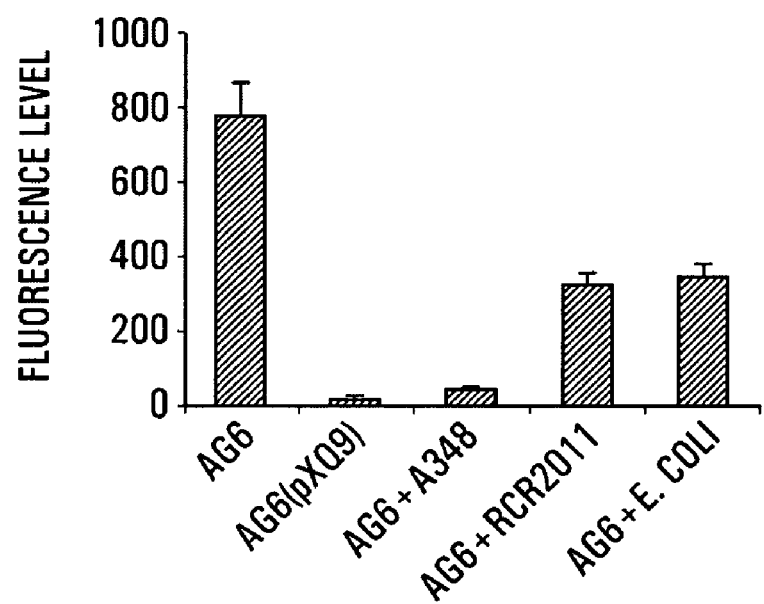

In the present study, the fully functional catalase gene katA repressed the katA-gfp expression at the highest level; thus it has the highest capacity to scavenge intracellular $H_2O_2$ (FIGS. 4, 7 and 10). Two mutant KatA proteins truncated at the C-terminus exhibited a very low level of accumulation in the cells and no significant catalase activity; neither repressed the katA-gfp expression at any significant level (FIGS. 7 and 8; Table 2). Thus, they have no significant capacity to scavenge intracellular $H_2O_2$. Two other mutant KatA proteins, KatA (98H/D) and KatA (94R/Q) (98H/D), could significantly repress the katA-gfp expression at a level much lower than the wild-type KatA (FIG. 7).

Incidentally, only these two mutant KatA proteins accumulated at a very high level in the bacteria (FIG. 6). This suggests that the sheer amount of the KatA proteins present in the cells might contribute to the repression, presumably because the mutant KatA proteins could still bind to $H_2O_2$ to reduce the availability of intracellular $H_2O_2$. KatA (98H/D) repressed the katA-gfp expression at a level slightly higher than KatA (94R/Q) (98H/D) (FIG. 7), presumably due to its low catalase activity while KatA (94R/Q) (98H/D) did not possess any significant catalase activity (Table 2). All of these indicate that this assay technology is extremely sensitive in determining the intracellular $H_2O_2$ scavenging capacities of different molecules and that this assay can analyze molecules that can scavenge intracellular $H_2O_2$ directly or indirectly.

EXAMPLE 14

Repression of katA-gfp Expression by Surrounding Bacterial Cells

To investigate whether the repression of katA-gfp expression could occur intercellularly, AG6 was co-cultured with the wild type stain A348 (see Example 7). As shown in FIG. 10, A348 indeed could repress the katA-gfp expression in the surrounding AG6 cells, when A348 was mixed with AG6 (upper panel). The fluorescence level of the A348+AG6 mixture was reduced about 20 fold as compared to that of AG6 alone (lower panel). Evaluation of the viable cell count of the AG6+A348 mixture showed that AG6 was 50% of the total cells as expected, suggesting that the repression in the mixture was caused intercellularly and not simply due to the dilution effect from the non-fluorescent A348 cells.

This intercellular repression phenomenon was also observed when AG6 was co-cultured with *R. meliloti* and *E. coli* which contained the catalase genes (Herouart et al, 1996; Loewen, 1997) and possessed the catalase activity as measured by the catalase activity assay. The repression of katA-gfp expression by *R. meliloti* and *E. coli* was weaker than that of A348 (FIG. 10), presumably because they grew slower than AG6 on IB plate as demonstrated by the viable cell count experiment. These suggest that $H_2O_2$ generated in AG6 could pass through the bacterial cell membranes and enter into the surrounding cells that possessed the catalase activity equivalent to KatA. The repression of katA-gfp expression could be achieved by catalases from other bacterial species. This indicates that intracellular $H_2O_2$ scavengers can be applied, external and adjacent to the cells under oxidative stress, in the form of live cells or non-living systems that can receive $H_2O_2$ from the adjacent cells under oxidative stress.

Interestingly, active catalase added to the medium of AG6 cells did not repress katA-gfp expression. Catalase purchased from Sigma was added into IB plates at a final concentration of 1 or 5 microgram per ml. AG6 cells (carrying the katA-gfp fusion) were then grown on the IB plate. The bacterial cells exhibited the same level of GFP expression as the AG6 cells grown in the absence of catalase. To ensure that the catalase in the IB medium was still active, hydrogen peroxide was dropped onto the catalase-containing plate. Air bubbles were instantly visible in the catalase-containing plate; no air bubble was found in the control catalase-free IB plate. This demonstrated that the catalase in the medium was active. Therefore, it can be concluded that extracellular catalase could not remove the intracellular hydrogen peroxide.

REFERENCES

Arnold et al. (2001) *Proc. Natl. Acad. Sci. USA*, 98(10): 5550-55.

Cangelosi, G. A., Best, E. A., Martinetti, G. and Nester, E. W. (1991) Genetic analysis of Agrobacterium. *Methods Enzymol* 204: 384-397.

Chalfie M. and Prashner D. C., U.S. Pat. No. 5,491,084.

Charles, T. C., and Nester, E. W. (1993) A chromosomally encoded two-component sensory transduction system is required for virulence of *Agrobacterium tumefaciens*. *J Bacteriol* 175: 6614-6625.

Chen, C. Y., and Winans, S. C. (1991) Controlled expression of the transcriptional activator gene virG in *Agrobacterium tumefaciens* by using the *Escherichia coli* lac promoter. *J Bacteriol* 173: 1139-1144.

Clare, D. A., Duong, M. N., Darr, D., Archibald, F. and Fridovich, I. (1984) Effects of molecular oxygen on detection of superoxide radical with nitroblue tetrazolium and on activity stains for catalase. *Anal Biochem* 140: 532-537.

Ditta, G., Stanfield, S., Corbin, D. and Helinski, D. R. (1980) Broad host range DNA cloning system for gram-negative bacteria: construction of a gene bank of *Rhizobium melioti*. *Proc Natl Acad Sci* 77: 7347-7351.

Farr et al., Microbiol. Rev., 55, pp. 561-85 (1991).

Farr U.S. Pat. No. 5,585,252.

Farr U.S. Pat. No. 5,811,231.

Farr U.S. Pat. No. 5,589,337.

Gonzalez-Flecha, B. and Demple, B. (1995) Metabolic sources of hydrogen peroxide in aerobically growing *Escherichia coli*. *J Biol Chem* 270: 13681-13687.

Gonzalez-Flecha, B. and Demple, B. (1997) Homeostatic regulation of intracellular hydrogen peroxide concentration in aerobically growing *Escherichia coli*. *J Bacteriol* 179:382-388.

Gort and Imlay, (1998) *J Bacteriol.* 1998 March 180(6): 1402-10.

Gould S. J., and Subramani S., *Anal Biochem.* 1988 November 15;175(1):5-13.

Greenberg et al., *Proc. Natl. Acad. Sci. USA,* 87, pp. 6181-85 (1990).

Gregory, E. M., and Fridovich, I. (1974) Visualization of catalase on acrylamide gels. *Anal Biochem* 58: 57-62

Herouart, D., Sigaud, S., Moreau, S., Frendo, P., Touati, D., and Puppo, A. (1996) Cloning and characterization of the katA gene of *Rhizobium meliloti* encoding a hydrogen peroxide-inducible catalase. *J Bacteriol* 178: 6802-6809.

Hillar, A., Peters, B., Pauls, R., Loboda, A., Zhang, H. Mauk, A. G., and Loewen, P. C. (2000) Modulation of the activities of catalase-peroxidase HPI of *Escherichia coli* by site-directed mutagenesis. *Biochemistry* 39:5868-5875.

Ho, S. N., Hunt, H. D., Horton, R. M., Pullen, J. K., and Pease, L. R. (1989) Site-directed mutagenesis by overlap extension using the polymerase chain reaction. *Gene* 77:51-59.

Kogoma et al., Proc. Natl. Acad. Sci USA, 85, pp. 4799-803 (1988).

Koh J., Enders G. H., et al, Nature. June 8; 375(6531):506-10 (1995).

Laemmli, U. K. (1970) Cleavage of structural proteins during the assembly of the head of bacteriophage T4. *Nature* 227: 680-685.

Li, L. P., Li, Y., Lim, T. M., and Pan, S. Q. (1999) GFP-aided confocal laser scanning microscopy can monitor *Agrobacterium tumefaciens* cell morphology and gene expression associated with infection. *FEMS Microbiol Lett* 179: 141-146.

Loewen, P. C. (1997) Bacterial catalases. In Oxidative stress and the molecular biology of antioxidant defenses. Scandalios, J. G. (eds). Cold Spring Harbor Laboratory Press, pp. 273-308.

Maciver, I., and Hansen, E. J. (1996) Lack of expression of the global regulator OxyR in *Haemophilus influenzae* has a profound effect on growth phenotype. *Infect Immun* 64: 4618-4629.

Mahadev et al. (2001) *J. Biol. Chem.* 15;276(24):21938-42.

Mohanty, J. Jonathan, G., Jaffe, S., Schulman E. S., and Raible, D. G. (1997) A highly sensitive fluorescent microassay of $H_2O_2$ release from activated human leukocytes using a dihydroxyphenoxazine derivative. *J Immunol Methods* 202: 133-141.

Murashige, T., and Skoog, F. (1962) A revised medium for rapid growth and bioassays with tobacco tissue cultures. *Physiol Plant* 15: 473-497.

Ren et al. (2002) *J. Biol. Chem.* 277(1):559-65.

Saliim and Abu-Shakra (2001) *Teratog Carcinog Mutagen* 21 (5):349-59.

Sambrook, J. F., Fritsch, E. F., and Maniatis, T. (1989) *Molecular Cloning: a laboratory manual,* 2nd ed. Cold Spring Harbor Laboratory, Cold Spring Harbor, N.Y.

Shapiro S. K., Chou J., et al., Gene November; 25: 71-82 (1983).

Suarez, A., Guttler, A., Stratz, M., Staendner, L. H., Timmis, K. N., and Guzman, C. A. (1997) Green fluorescent protein-based reporter systems for genetic analysis of bacteria including monocopy applications. *Gene* 196: 69-74.

Thiel G., Petersohn D., and Schoch S., Gene February 12; 168: 173-176 (1996).

Xu, X. Q. and Pan, S. Q. (2000) An Agrobacterium catalase as a virulence factor involved in tumorigenesis. *Mol Microbiol* 2:407-14.

While a number of embodiments have been presented, it is apparent that the basic construction can be altered to provide other embodiments which utilize the methods and kits of the invention. The scope of the invention is to be defined by the claims appended hereto rather than the specific embodiments presented herein by way of example.

The invention claimed is:

1. A method for determining the ability of a compound to remove a reactive oxygen species (ROS), comprising:
   a) providing a cell of *Agrobacterium tumefaciens* that is genetically modified to provide a constitutively elevated level of said ROS and comprising a promoter of a KatA gene that is inducible by H2O2 and is operably linked to a reporter gene, wherein the reporter gene is heterologous to the KatA gene promoter,
   b) exposing the cell to a compound potentially able to remove the ROS;
   c) measuring change in ROS-inducible expression of the reporter gene in the cell when exposed to the compound, wherein the KatA promoter is induced by exposing the cell to acidic culture conditions before step (c).

2. A method for selecting a nucleic acid encoding a protein which is able to remove a reactive oxygen species (ROS), from a plurality of nucleic acids, the method comprising:

a) providing *Agrobacterium tumefaciens* cells that are genetically modified to provide a constitutively elevated level of said ROS and comprising a promoter of a KatA gene that is inducible by H2O2 and is operably linked to a reporter gene, wherein the reporter gene is heterologous to the KatA gene promoter;

b) introducing into the cells expression vectors comprising a plurality of nucleic acids encoding proteins which are potentially able to remove the ROS;

c) measuring change in the ROS-inducible expression of the reporter gene in the cells when nucleic acids are expressed;

d) selecting for cells with reduced ROS-inducible expression of the reporter gene; and e) isolating nucleic acids from the cells with reduced expression of the reporter gene; wherein the isolated nucleic acids encodes a protein able to remove the ROS; wherein the KatA promoter is induced by exposing the cell to acidic culture conditions before step (c).

3. The method of claim 1, wherein the step of exposing the cell to the compound comprises providing the compound externally to the cell.

4. The method of claim 1, wherein the step of exposing the cell to the compound comprises expressing the compound from a nucleic acid inside the cell.

5. The method of claim 1, wherein the cell lacks a gene encoding an active enzyme selected from the group consisting of: catalase, superoxide dismutase, alkyl hydroperoxidase, and glutathione reductase.

6. The method of claim 5 wherein the active enzyme is catalase.

7. A diagnostic kit for determining the ability of a gene product to remove a reactive oxygen species (ROS), the kit comprising:

a) an *Agrobacterium tumefaciens* cell that is genetically modified to provide a constitutively elevated level of said ROS comprising a promoter of a KatA gene that is inducible by H2O2 and is operably linked to a reporter gene, wherein the reporter gene is heterologous to the KatA gene promoter, b) means for introducing into the cell a nucleic acid encoding a gene product potentially able to remove the ROS; and c) instruction for determining a reduction in expression of the reporter gene in cell of (a) when the nucleic acid is expressed, thereby determining whether the gene product is able to remove the ROS, said instruction further includes instructing a step of inducing the KatA promoter by exposing the cell to acidic conditions, before step (c).

8. The diagnostic kit of claim 7, wherein the reporter gene encodes a reporter product, and wherein the kit further comprises means for measuring the reporter product.

9. The kit of claim 7, further comprising means for elevating the intracellular level of the ROS in the cell.

10. The kit of claim 7, wherein the cell lacks a gene encoding an active enzyme selected from the group consisting of: catalase, superoxide dismutase, alkyl hydroperoxidase, and glutathione reductase.

11. The kit of claim 10, wherein the active enzyme is catalase.

12. The method of claim 2, wherein the cell lacks a gene encoding an active enzyme selected from the group consisting of: catalase, superoxide dismutase, alkyl hydroperoxidase, and glutathione reductase.

13. The method of claim 12, wherein the active enzyme is catalase.

14. The method claim 2, wherein the reporter gene encodes a protein functional in the bacterial cell.

* * * * *